United States Patent
Besso et al.

(10) Patent No.: US 12,342,861 B2
(45) Date of Patent: Jul. 1, 2025

(54) AEROSOL-GENERATING SYSTEM AND ARTICLE FOR USE THEREWITH

(71) Applicant: PHILIP MORRIS PRODUCTS S.A., Neuchatel (CH)

(72) Inventors: Clement Besso, Neuchatel (CH); Nazan Gunduz, Le Mont sur Lausanne (CH)

(73) Assignee: Philip Morris Products S.A., Neuchatel (CH)

( * ) Notice: Subject to any disclaimer, the term of this patent is extended or adjusted under 35 U.S.C. 154(b) by 514 days.

(21) Appl. No.: 17/436,435

(22) PCT Filed: Mar. 4, 2020

(86) PCT No.: PCT/EP2020/055743
§ 371 (c)(1),
(2) Date: Sep. 3, 2021

(87) PCT Pub. No.: WO2020/182585
PCT Pub. Date: Sep. 17, 2020

(65) Prior Publication Data
US 2022/0175030 A1    Jun. 9, 2022

(30) Foreign Application Priority Data
Mar. 8, 2019    (EP) .................................. 19161774

(51) Int. Cl.
*A24F 40/42*    (2020.01)
*A24F 40/20*    (2020.01)
(Continued)

(52) U.S. Cl.
CPC .............. *A24F 40/42* (2020.01); *A24F 40/20* (2020.01); *A24F 40/485* (2020.01); *A24F 40/53* (2020.01)

(58) Field of Classification Search
CPC ........ A24F 40/42; A24F 40/53; A24F 40/485; A24F 40/20
(Continued)

(56) References Cited

U.S. PATENT DOCUMENTS

| 4,922,901 A | * | 5/1990 | Brooks | ............... A61M 16/109 131/273 |
| 4,947,874 A | * | 8/1990 | Brooks | ................... A24F 40/50 131/194 |

(Continued)

FOREIGN PATENT DOCUMENTS

| CA | 3002423 | 4/2017 |
| CN | 104824850 | 8/2015 |

(Continued)

OTHER PUBLICATIONS

PCT Search Report and Written Opinion for PCT/EP2020/055743 dated May 27, 2020 (10 pages).
(Continued)

*Primary Examiner* — Gary F Paumen
(74) *Attorney, Agent, or Firm* — Mueting Raasch Group

(57) ABSTRACT

An aerosol-generating system comprising: an aerosol-generating article (1), the aerosol-generating article comprising a single metered dose of an aerosol-forming substrate; an airflow pathway (108) arranged between an air inlet (110) and an air outlet (112); an aerosolisation chamber (116) arranged at a location along the airflow pathway (108) such that the airflow pathway passes through at least a portion of the aerosolisation chamber (116); and a flow controller (122, 124) for selectively controlling the flow of air through the airflow pathway (108), the flow controller (122, 124) having an open configuration in which air can flow into and out of the aerosolisation chamber (116) and a closed configuration in which air is substantially prevented from flowing into and out of the aerosolisation chamber (116); wherein the aero- (Continued)

solisation chamber (116) is configured to open to receive only one aerosol-generating article (1) at a time; wherein the aerosolisation chamber (116) is configured to close to contain the aerosol-generating article (1); the aerosol-generating system further comprising a heating element (118, 120) arranged to heat the aerosolisation chamber (116) when an aerosol-generating article (1) is received within the aerosolisation chamber (116); wherein the aerosol-generating system is configured to heat the aerosolisation chamber (116) containing the aerosol-generating article (1) only when the flow controller (122, 124) is in the closed configuration.

15 Claims, 7 Drawing Sheets

(51) Int. Cl.
  *A24F 40/485* (2020.01)
  *A24F 40/53* (2020.01)
(58) Field of Classification Search
  USPC .......................................................... 131/329
  See application file for complete search history.

(56) References Cited

U.S. PATENT DOCUMENTS

| | | | | |
|---|---|---|---|---|
| 5,060,671 | A * | 10/1991 | Counts | A24F 40/50 |
| | | | | 131/273 |
| 5,865,185 | A * | 2/1999 | Collins | H05B 3/24 |
| | | | | 131/194 |
| 5,934,289 | A * | 8/1999 | Watkins | A24F 40/46 |
| | | | | 131/194 |
| 12,041,968 | B2 | 7/2024 | Egoyants | |
| 2003/0111088 | A1 | 6/2003 | Fox | |
| 2012/0298123 | A1 * | 11/2012 | Woodcock | A24B 15/186 |
| | | | | 131/328 |
| 2013/0192621 | A1 * | 8/2013 | Li | H05B 3/0014 |
| | | | | 131/329 |
| 2014/0261488 | A1 * | 9/2014 | Tucker | A24F 40/50 |
| | | | | 131/328 |
| 2015/0027455 | A1 * | 1/2015 | Peleg | A24F 40/30 |
| | | | | 131/328 |
| 2015/0040930 | A1 * | 2/2015 | Robinson | A24F 40/42 |
| | | | | 131/329 |
| 2015/0335070 | A1 | 11/2015 | Sears | |
| 2016/0174610 | A1 * | 6/2016 | Kuczaj | A24F 40/57 |
| | | | | 392/394 |
| 2016/0325858 | A1 * | 11/2016 | Ampolini | B65B 59/001 |
| 2017/0367409 | A1 | 12/2017 | Thorens | |
| 2018/0020733 | A1 * | 1/2018 | Jochnowitz | F22B 1/284 |
| | | | | 131/329 |
| 2018/0154092 | A1 * | 6/2018 | Patoret | A24F 40/42 |
| 2018/0292250 | A1 * | 10/2018 | Colotte | A24F 40/53 |
| 2018/0303161 | A1 * | 10/2018 | Bilat | A24B 15/167 |
| 2018/0317557 | A1 | 11/2018 | Monsees | |

FOREIGN PATENT DOCUMENTS

| | | | | |
|---|---|---|---|---|
| KR | 10-2014-0068807 | | 6/2014 | |
| WO | WO 2014/102095 | | 7/2014 | |
| WO | WO 2015/082652 | | 6/2015 | |
| WO | WO-2015112750 | A1 * | 7/2015 | ............ A24F 40/46 |
| WO | WO 2016/001921 | | 1/2016 | |
| WO | WO 2017/068092 | | 4/2017 | |
| WO | WO 2017/068093 | | 4/2017 | |
| WO | WO 2017/068099 | | 4/2017 | |
| WO | WO 2018/007563 | | 1/2018 | |
| WO | WO-2018019578 | A1 * | 2/2018 | ........... A24B 15/167 |
| WO | WO 2018/122060 | | 7/2018 | |
| WO | WO 2018/122070 | | 7/2018 | |
| WO | WO 2018/122095 | | 7/2018 | |
| WO | WO 2018/122097 | | 7/2018 | |
| WO | WO 2020/044179 | | 3/2020 | |
| WO | WO 2020/044181 | | 3/2020 | |

OTHER PUBLICATIONS

Extended European Search Report for Application No. 19161774.5 dated Sep. 20, 2019.
Notice of Allowance issued in Korea for Application No. 2021-7029206 dated Apr. 24, 2025 (4 pages). English translation included.

* cited by examiner

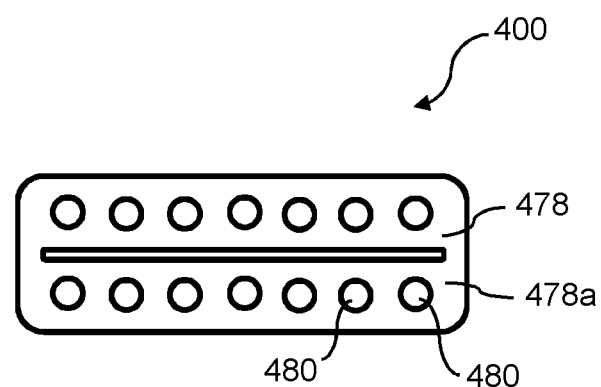
FIG. 8
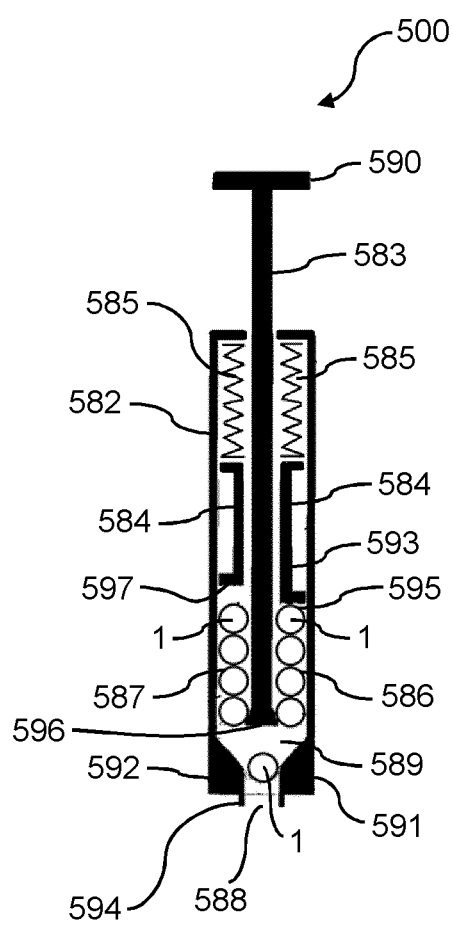  
FIG. 9A    FIG. 9B    FIG. 9C

AEROSOL-GENERATING SYSTEM AND ARTICLE FOR USE THEREWITH

This application is a U.S. National Stage Application of International Application No. PCT/EP2020/055743 filed Mar. 4, 2020, which was published in English on Sep. 17, 2020, as International Publication No. WO 2020/182585 A1. International Application No. PCT/EP2020/055743 claims priority to European Application No. 19161774.5 filed Mar. 8, 2019.

The present invention relates to an aerosol-generating system, to a device for use with the system and to a method of generating an aerosol. In particular, the invention relates to handheld aerosol-generating systems and devices which vaporise an aerosol-forming substrate by heating to generate an aerosol to be puffed or inhaled by a user.

Handheld electrically operated aerosol-generating devices and systems are known that consist of a device portion comprising a battery and control electronics, a portion for containing or receiving an aerosol-forming substrate and an electrically operated heater for heating the aerosol-forming substrate to generate an aerosol. A mouthpiece portion is also included on which a user may puff to draw aerosol into their mouth.

Some devices and systems use a liquid aerosol-forming substrate or e-liquid stored in a liquid storage portion. Such devices typically use a wick to carry the liquid aerosol-forming substrate from the liquid storage portion to the heater where it is aerosolised. A problem with such devices is that they may not provide accurate measurements of the amount of aerosol generated during use and, in particular, the amount of aerosol generated per puff. Consequently, a user does not have insight into their consumption of aerosol or the various components in the aerosol, which therefore makes it difficult for a user to control the amount of aerosol or aerosol components they receive per unit of time or per puff. Whilst the total amount of liquid aerosol-forming substrate in the liquid storage portion may be known and therefore the total quantity of aerosol received once the liquid storage portion is empty can be roughly estimated, such systems and devices do not provide an indication of the amount of aerosol received per puff.

There are a number of parameters which determine the quantity of aerosol generated per puff in a device using a liquid aerosol-forming substrate, for example, the amount of liquid reaching the heating area, which is related to the capillarity effect of the wick, the thickness of the wick, the distance from the liquid storage portion to the heater and the viscosity of the liquid. Further parameters which affect the amount of aerosol generated include, the reactivity of the device to a puff command, how quickly the heater reaches its working temperature and the value of such working temperature. In addition to these intrinsic parameters of the device, other parameters relating to the condition and use of the device also have an impact on the amount of aerosol generated, for example, the physical orientation of the device, the remaining quantity of liquid in the liquid storage portion (which affects the length of the travel of liquid in the wick and whether the wick is wet or dry), the duration of time since the device was previously used, the duration of the puff and the ambient temperature. Such parameters make it difficult to determine reliably the amount of aerosol or aerosol components consumed per puff.

Other types of aerosol-generating devices and systems use a solid aerosol-forming substrate such as a tobacco material. Such devices may comprise a recess for receiving a cigarette-shaped rod comprising folded sheets of such a tobacco material. A blade-shaped heater arranged in the recess is inserted into the centre of the rod as the rod is received in the recess. The heater is configured to heat the tobacco material to generate an aerosol.

The amount of aerosol generated by such devices is also determined by certain parameters, for example, the density distribution of the tobacco sheets around the heater, the orientation of the folded tobacco sheets relative to the heater and the way in which heat spreads into the tobacco rod and the duration of use. The tobacco sheets closest to the heater blade may be heated differently from the tobacco sheets furthest from the heater, which may result in a variability of the amount of aerosol generated over time as well as possible overheating of the tobacco sheets closest to the heater.

It would be desirable to provide an aerosol-generating device which provides for a more reliable determination of the amount of aerosol generated. It would be desirable to provide an aerosol-generating device which would allow a user to more accurately control their consumption of aerosol, or one or more aerosol components, or their consumption of both aerosol and one or more aerosol components. It would be desirable to provide an aerosol-generating system which provides for a more reliable determination of the amount of aerosol generated. It would be desirable to provide an aerosol-generating system which would allow a user to more accurately control their consumption of aerosol or their consumption of one or more aerosol components. It would be desirable to provide a method for generating an aerosol, which method provides for a more reliable determination of the amount of aerosol generated. It would be desirable to provide method for generating an aerosol, which method would allow a user to more accurately control their consumption of aerosol or one or more aerosol components.

According to an aspect of the invention, there is provided an aerosol-generating system. The aerosol-generating system may comprise an aerosol-generating article. The aerosol-generating article may comprise a single metered-dose of an aerosol-forming substrate. The aerosol-generating system may comprise an airflow pathway arranged between an air inlet and an air outlet. The aerosol-generating system may comprise an aerosolisation chamber arranged at a location along the airflow pathway such that the airflow pathway passes through at least a portion of the aerosolisation chamber. The aerosol-generating system may comprise a flow controller for selectively controlling the flow of air through the airflow pathway. The flow controller may comprise an open configuration in which air can flow into and out of the aerosolisation chamber and a closed configuration in which air is substantially prevented or blocked from flowing into and out of the aerosolisation chamber. The aerosolisation chamber may be configured to receive only one aerosol-generating article at a time. The aerosol-generating system may comprise a heating element. The heating element may be arranged to heat the aerosol-generating article when received within the aerosolisation chamber. The aerosol-generating system may be configured to heat the aerosol-generating article only when the flow controller is in the closed configuration.

According to an aspect of the invention, there is provided an aerosol-generating system comprising: an aerosol-generating article, the aerosol-generating article comprising a single metered-dose of an aerosol-forming substrate; an airflow pathway arranged between an air inlet and an air outlet; an aerosolisation chamber arranged at a location along the airflow pathway such that the airflow pathway passes through at least a portion of the aerosolisation chamber; and a flow controller for selectively controlling the flow of air through the airflow pathway, the flow controller having an open configuration in which air can flow into and out of the aerosolisation chamber and a closed configuration in which air is substantially blocked from flowing into and out of the aerosolisation chamber; wherein the aerosolisation chamber is configured to receive only one aerosol-generating article at a time; the system further comprising a heating element arranged to heat the aerosol-generating article within the aerosolisation chamber; wherein the aerosol-generating system is configured to heat the aerosol-generating article only when the flow controller is in the closed configuration.

As used herein, the term 'aerosol-generating system' relates to a system that interacts with an aerosol-forming substrate to generate an aerosol.

As used herein, the term 'aerosol-generating article' relates to an article comprising an aerosol forming substrate. Optionally, the aerosol-generating article may also comprise one or more further components, such as a carrier material, wrapper, etc.

As used herein, the term "metered-dose" refers to an aerosol-generating article which has a measured or predetermined amount of an aerosol-forming substrate. The metered dose corresponds to a dose of aerosol-forming substrate to be delivered to a user during a single inhalation or puff. The metered dose of aerosol-forming substrate includes a component or components required to generate an aerosol. For example, the metered dose may comprise a predetermined amount of tobacco or nicotine or a flavourant or a combination of these. The metered dose may also comprise an aerosol-former.

As used herein, the term 'aerosol-forming substrate' relates to a substrate capable of releasing one or more volatile compounds that can form an aerosol. Such volatile compounds may be released by heating the aerosol-forming substrate. An aerosol-forming substrate may conveniently be part of an aerosol-generating device or system.

The system allows a user to accurately determine and control the dose of aerosol-forming substrate that can be administered. Each aerosol-generating article comprises a single metered-dose of an aerosol-forming substrate. When the user uses the device, the user knows how much aerosol-forming substrate the aerosol-generating article comprises and therefore how much aerosol or how much of one or more aerosol components they receive. The amount of aerosol generated and hence the aerosol components is fixed by the aerosol-generating article having a metered-dose or predetermined amount of aerosol-forming substrate.

The aerosol-generating article is a single-use article. As used herein, the term 'single-use' refers to an aerosol-generating article which is configured to be used for only a single puff or inhalation before being discarded. Each time a user takes a puff or inhales via the aerosol-generating system, a fresh aerosol-generating article is used. This provides for highly repeatable generation of aerosol and reduces the variability in aerosol generation which may be encountered over successive uses of a multiple-use aerosol-generating article, that is an aerosol-generating article having sufficient aerosol-forming substrate for more than one use.

When using a multiple-use aerosol-generating article, there may be variability in the amount of aerosol a user may take over successive uses of the article. However, when using the system of the invention, for each use or puff, the user can only take a dose of aerosol components up to the metered-dose of aerosol-forming substrate provided by the aerosol-generating article. In other words, the maximum dose that a user can receive per use or puff is determined by the metered-dose of aerosol-forming substrate. Even if the user attempts to use the aerosol-generating article a second time, the maximum dose is still limited to the metered-dose of aerosol-forming substrate.

The system also has a flow controller which has a closed configuration to substantially block or inhibit air from entering or leaving the aerosolisation chamber during heating. The flow controller may inhibit generated aerosol from leaking out of the aerosolisation chamber during heating. The system therefore heats the aerosol-generating article in a closed system until the aerosol-forming substrate has been aerosolised. Consequently, when the system is ready for a user to take a puff, the user knows how much aerosol or aerosol components they are going to receive. Furthermore, since the aerosol-generating article is a single-use article and the aerosol generated can be consumed with a single puff, any leakage of aerosol which may otherwise occur between puffs, for example, with a multiple-use aerosol-generating article, may be reduced. This provides improved insight and further control over the amount of aerosol and aerosol components being consumed. Once used, the single-use aerosol-generating article can then be discarded and replaced with a fresh article.

The aerosol-generating system may be configured to heat the aerosolisation chamber when an aerosol-generating article is received within the aerosolisation chamber such that substantially all of the aerosol-generating substrate is aerosolised. As used herein, the term "substantially all" is intended to mean that at least 90 percent of the aerosol-forming substrate is aerosolised, more particularly at least 95 percent of the aerosol-forming substrate is aerosolised, more particularly at least 98 percent of the aerosol-forming substrate is aerosolised and yet more particularly at least 99 percent of the aerosol-forming substrate is aerosolised.

The aerosolisation chamber may be configured to open to receive the aerosol-generating article. The aerosolisation chamber may be configured to close to contain the aerosol-generating article. Closing the aerosolisation chamber also assists in retaining generated aerosol in the aerosolisation chamber during heating until a user is ready to take a puff.

The aerosolisation chamber is configured to receive only one single-use aerosol-generating article at a time. The aerosolisation chamber may be configured to receive only one single-use aerosol-generating article at a time by being sized, shaped or dimensioned to accommodate only one aerosol-generating article. For example, in the case of a substantially spherical aerosol-generating article such as a spherical bead or pellet, the dimensions of the aerosolisation chamber may be less than 2 times the diameter of the aerosol-generating article and more particularly less than 1.5 times the diameter of the aerosol-generating article. This would prevent more than one article from being placed in the aerosolisation chamber because if there was already an article in the aerosolisation chamber there would be insufficient space to insert another. The shape, size or dimension relationship between the aerosol-generating article and the aerosol-generating system may also permit air to flow around the article in the aerosolisation chamber. This may cause some movement of the aerosol-generating article within the aerosolisation chamber. This may provide effective entrainment of the aerosol within the moving airflow. The moving aerosol-generating article may also generate sound as it moves or "rattles" within the aerosolisation chamber. This may provide audible feedback to a user that air is flowing through the aerosolisation chamber as they are taking a puff or inhaling.

Alternatively, the aerosolisation chamber may be configured to receive only one single-use aerosol-generating article at a time by having a sensor to detect the number of aerosol-generating articles in the aerosolisation chamber. The sensor may comprise, for example, a capacitive sensor or an inductive sensor for respectively detecting the different electric or electromagnetic fields created by there being more than one article in the aerosolisation chamber. Optionally, the aerosol-generating system may comprise one or more counters for counting the number of articles entering the aerosolisation chamber and the number of articles leaving the aerosolisation chamber. Such counters could be incremented by a signal generated by activating a sensor, such as microswitch or light sensor. Control circuitry may be configured to deactivate or disable the aerosol-generating system if it detects more than one aerosol-generating article in the aerosolisation chamber until the number of articles is reduced to one.

Alternatively, aerosolisation chamber may be configured to receive only one single-use aerosol-generating article at a time by a delivery mechanism which only allows one article to be delivered to the aerosolisation chamber at a time, for example by always ejecting a used article prior to inserting a new one or by ejecting a used article as part of the step of inserting a new article.

The cross-sectional area of the aerosol-generating article may be less than a cross-sectional area of the aerosolisation chamber. This may enable air can flow around the aerosol-generating article and through the aerosolisation chamber. Here, cross-sectional area is taken as being the cross-sectional area of the aerosol-generating article or the aerosolisation chamber in a plane perpendicular to the average direction of airflow through the aerosolisation chamber. In the aerosolisation chamber, the average direction of airflow is generally a substantially straight-line between the points at which the airflow pathway enters and exits the aerosolisation chamber.

In the case of a substantially spherical aerosol-generating article such as a spherical bead or pellet, at least one cross-sectional dimension of the aerosolisation chamber, in a direction perpendicular to the average direction of airflow through the aerosolisation chamber, may be larger than the diameter of the aerosol-generating article such that air can flow around the aerosol-generating article and through the aerosolisation chamber. This also allows the article to move around within chamber, which helps to entrain the aerosol in the airflow. Such movement may make a noise which would provide audible feedback, such as a rattling noise, to a user that air is flowing through the aerosolisation chamber.

The cross-sectional area of the aerosol-generating article may be between about 60 percent and 90 percent of the cross-sectional area of the aerosolisation chamber. This has been found to be a suitable range for allowing air to flow around the aerosol-generating article and through the aerosolisation chamber. It also allows sufficient movement of the article within the aerosolisation chamber.

The aerosolisation chamber may comprise an aperture through which an aerosol-generating article can be loaded into the aerosolisation chamber, the system further comprising a closure for closing the aperture during heating of the aerosol-generating article. This arrangement allows an aerosol-generating article to be inserted into the aerosolisation chamber and the closure prevents any aerosol escaping from the aerosolisation chamber until a user is ready to take a puff or inhalation.

The system may further comprise a delivery mechanism for delivering an aerosol-generating article into the aerosolisation chamber. The delivery mechanism may engage or encompass at least one aperture formed in the aerosolisation chamber. The delivery mechanism may allow an aerosol-generating article to be delivered to the aerosolisation chamber. The delivery mechanism may eject a used article prior to, or at the same time as, inserting a fresh article into the aerosolisation chamber. The delivery mechanism may comprise a drawer mechanism. The delivery mechanism may comprise a slider mechanism. The drawer mechanism and slider mechanism may comprise resiliently biased doors.

In the case where the aerosol-generating article comprises a sheet or a strip of absorbent carrier material coated with or impregnated with aerosol-forming substrate (as described below), the delivery mechanism may, in some embodiments, comprise a suitably shallow drawer mechanism or a slide for gripping the aerosol-generating article by at least one of it edges.

The aerosol-generating system may comprise a guard for preventing the aerosol-generating article from leaving or escaping from the aerosolisation chamber via the airflow pathway. The guard may prevent the aerosol-generating article from leaving the aerosolisation chamber both prior to heating and after heating. In other words, the guard may prevent the aerosol-generating article from leaving the aerosolisation chamber both in the preheated or pre-aerosolised state of the aerosol-generating article and in the post-heated or post-aerosolised state of the aerosol-generating article. The dimensions of the aerosol-generating article may be smaller in the post-heated state due to the loss of aerosol-forming substrate. For example, in embodiments where the aerosol-generating article is a substantially spherical bead comprising a core coated with aerosol-forming substrate (as described below), the guard may be configured to prevent both the bead and the core from leaving the aerosolisation chamber via the airflow pathway.

Optionally, the guard may comprise a reduction in the cross-sectional area of the airflow pathway at the point the aerosolisation chamber is joined to the remainder of the airflow pathway. That is, the cross-sectional area of the airflow pathway outside of the aerosolisation chamber may be smaller than the cross-sectional area of the aerosolisation chamber. In some embodiments, the airflow pathway may have a constriction at the point the aerosolisation chamber is joined to the remainder of the airflow pathway. In the case of a spherical aerosol-generating article, at least one cross-sectional dimension of the airflow pathway outside the aerosolisation chamber may, in some embodiments, be smaller than a diameter of the aerosol-generating article. This may prevent the aerosol-generating article from leaving the aerosolisation chamber via the airflow pathway The cross-sectional dimension may be a cross-sectional dimension in a direction perpendicular to the average direction of airflow through the airflow pathway.

Optionally, the guard may comprise a guard member arranged across at least a portion of the airflow pathway. For example, the guard may comprise a mesh, a plate having at least one hole formed therethrough, a baffle, a hook, a protrusion or another suitable physical obstruction to prevent the aerosol-generating article from leaving the aerosolisation chamber.

Clearly it is more important to have a guard at the downstream side of the aerosolisation chamber to prevent the aerosol-generating article from entering the downstream portion of the airflow pathway and being inhaled by a user via a mouthpiece arranged at the air outlet. However, a guard may be arranged on both the upstream and downstream sides of the aerosolisation chamber to prevent the aerosol-generating article from passing into the upstream and downstream portions of the airflow pathway.

The system may further comprise a storage unit for storing a plurality of aerosol-generating articles. The storage unit may comprise a blister pack or a reservoir. The storage unit may be integral to an aerosol-generating device or may be separate to the device for use within the aerosol-generating system.

The storage unit may comprise an injector-type dispenser or pen for storing and dispensing aerosol-generating articles. In some embodiments, the dispenser may comprise: a housing defining an exit orifice. A rod may be at least partially disposed within the housing. The rod may have an engagement face at a first end. The engagement face may be for engaging an aerosol-generating article. The rod may be movable between a retracted position and an extended position. The retracted position may be a position in which the engagement face of the rod is fully disposed within the housing. The extended position may be a position in which the engagement face of the rod is disposed outside the housing. When the rod is moved between the retracted position and the extended position, the engagement face of the rod may pass through the exit orifice. The dispenser may comprise a loading zone for accommodating a single aerosol-generating article when the rod is in the retracted position. The loading zone may be disposed between the exit orifice and the engagement face of the rod when the rod is in the retracted position. Optionally, the injector-type dispenser may be part of an aerosol-generating device. Optionally, the injector-type dispenser may be releasably engageable with the aerosol-generating device.

The aerosol-generating article may have a central symmetry. This allows a repeatable amount of aerosol to be generated regardless of the article's position in an aerosolisation chamber. The shape of the aerosol-generating article may also permit air to flow around the article in the aerosolisation chamber and some movement within the aerosolisation chamber. This provides effective entrainment of the aerosol within the moving airflow. The moving article may also generate sound as it moves or "rattles" within the aerosolisation chamber which may provide audible feedback to a user that air is flowing through the aerosolisation chamber as they are taking a puff or inhaling.

The aerosol-generating article may comprise a substantially spherical or ball-shaped bead or pellet. However, the article may have other suitable shapes, for example, a lozenge-shape or a cuboid or a cube shape.

The aerosol-generating article may comprise a core coated with an aerosol-forming substrate. For example, the core may comprise a substantially spherical bead or pellet. The core may be made from a heat-resistant material. The core may be made from an inert material. The core may be made from both a heat-resistant and an inert material. As used herein, the term "heat-resistant" refers to a core material which can be heated to the aerosolisation temperature of the aerosol-forming substrate without undergoing any appreciable structural change or other adverse transformation. The aerosolisation temperature of the aerosol-forming substrate may be less than 500° C. The aerosolisation temperature of the aerosol-forming substrate may be less than 450° C. The aerosolisation temperature of the aerosol-forming substrate may be less than 400° C. The aerosolisation temperature of the aerosol-forming substrate may be less than 350° C. The aerosolisation temperature of the aerosol-forming substrate may be less than 300° C. The term "inert" is taken to mean that the core material can be heated to the aerosolisation temperature of the aerosol-forming substrate without undergoing any appreciable chemical change or releasing unwanted by-products. The core may be formed from glass, metallic or a ceramic material. For example, the core may comprise a glass sphere. Preferably, the core material is smooth and non-permeable or non-porous so that the aerosol-forming substrate is only located on the surface of the core. This makes it easier to accurately control the amount of aerosol-forming substrate deposited on the surface of the core and reduces variability between beads. Furthermore, an impermeable or non-porous core means that air does not enter the core and can only flow around the outside of the core rather than through it. This helps to reduce variability in the amount of generated aerosol caused by, for example, the air carrying the aerosol leaving a portion of the aerosol inside the core or condensation of the aerosol forming in cooler internal parts of the core. Preferably, the core material is not fibrous.

In some embodiments, the aerosol-generating article may be configured for inductive heating (as will be described in more detail below). In the case of aerosol-generating articles intended for inductive heating, in some embodiments, the core material may comprise a susceptor material. The term "susceptor" is used herein to refer to a material that is capable of being inductively heated. That is, a susceptor material is capable of absorbing electromagnetic energy and converting it to heat. The susceptor material may comprise a ferromagnetic material. The susceptor material may comprise a ferrite material. The susceptor material may comprise a metallic material. The susceptor material may comprise at least one of ferritic iron, ferromagnetic steel, stainless steel, and aluminium.

In embodiments in which the susceptor material comprises stainless steel, the susceptor material may, in some embodiments, comprise at least one 400 series stainless steel. Suitable 400 series stainless steels include grade 410, grade 420, and grade 430.

In some embodiments, the core may be only partially covered with an aerosol-forming substrate. For example, the core may be coated with patches of aerosol-forming substrate. In some embodiments, the core may be completely coated with an aerosol-forming substrate. The coating of aerosol-forming substrate on the core may have a substantially uniform thickness. The coating of aerosol-forming substrate may be provided having a predetermined thickness. The thickness of the aerosol-forming substrate may range from 0.1 mm to 1.2 mm.

The aerosol-forming substrate may comprise a solid. The aerosol-forming substrate may comprise a liquid. The aerosol-forming substrate may comprise a gel. The aerosol-forming substrate may comprise any combination of two or more of a solid, a liquid and a gel.

The aerosol-forming substrate may comprise nicotine, a nicotine derivative or a nicotine analogue. The aerosol-forming substrate may comprise one or more nicotine salt. The one or more nicotine salt may be selected from the list consisting of nicotine citrate, nicotine lactate, nicotine pyruvate, nicotine bitartrate, nicotine pectates, nicotine aginates, and nicotine salicylate.

The aerosol-forming substrate may comprise an aerosol former. As used herein, an "aerosol former" is any suitable known compound or mixture of compounds that, in use, facilitates formation of a dense and stable aerosol and that is substantially resistant to thermal degradation at the operating temperature of the aerosol-generating article. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol formers are polyhydric alcohols or mixtures thereof, such as triethylene glycol, 1,3-butanediol and glycerine.

The aerosol-forming substrate may further comprise a flavourant. The flavourant may comprise a volatile flavour component. The flavourant may comprise menthol. As used herein, the term 'menthol' denotes the compound 2-isopropyl-5-methylcyclohexanol in any of its isomeric forms. The flavourant may provide a flavour selected from the group consisting of menthol, lemon, vanilla, orange, wintergreen, cherry, and cinnamon. The flavourant may comprise volatile tobacco flavour compounds which are released from the substrate upon heating.

The aerosol-forming substrate may further comprise tobacco or a tobacco containing material. For example, the aerosol-forming substrate may comprise any of: tobacco leaf, fragments of tobacco ribs, reconstituted tobacco, homogenised tobacco, extruded tobacco, tobacco slurry, cast leaf tobacco and expanded tobacco. Optionally, the aerosol-forming substrate may comprise tobacco powder compressed with an inert material, for example, glass or ceramic or another suitable inert material.

In cases where the aerosol-forming substrate comprises a liquid or a gel, in some embodiments, the aerosol-generating article may comprise an absorbent carrier. The aerosol-forming substrate may be coated on or impregnated into the absorbent carrier. For example, the nicotine compound and the aerosol-former may be combined with water as a liquid formulation. The liquid formulation may, in some embodiments, further comprise a flavourant. Such a liquid formulation may then be absorbed by the absorbent carrier or coated onto the surface of the carrier. The absorbent carrier may be a sheet of cellulosic-based material onto which the nicotine compound and the aerosol former may be coated or absorbed. For example, the absorbent carrier may be a sheet or strip of paper.

The aerosol-generating article may comprise an amount of aerosol-forming substrate sufficient for generating an amount of aerosol for only a single puff or inhalation or dose. An average puff volume for an adult user will depend on the type of device and aerosol-generating article being used but is typically in the range of about 35 ml to 550 ml. Optionally, the aerosol-forming substrate may comprise about 2 to 30 mg of tobacco, more particularly about 3 to 20 mg of tobacco, more particularly about 3 to 9 mg of tobacco and yet more particularly about 4 to 8 mg of tobacco. Optionally, the aerosol-forming substrate may comprise about 80 to 120 µg, more particularly about 90 to 110 µg, and yet more particularly about 100 µg, of nicotine, a nicotine derivative or a nicotine analogue. Optionally, the aerosol-forming substrate may comprise about 6 to 20% aerosol-former by weight. Optionally, the aerosol-forming substrate may comprise about 300 to 1250 µg and more particularly about 675 to 875 µg of aerosol former. These have been found to be suitable amounts of tobacco, nicotine and aerosol-former respectively for a single puff or inhalation or dose. In the case of an aerosol-generating article comprising an absorbent carrier such as paper, the paper may be perforated or marked to indicate to a user a quantity equivalent to a single puff or inhalation or individual doses.

The aerosol-generating article may comprise a plurality of particles compressed into a bead or pellet, the bead or pellet being configured to disintegrate upon heating to a predetermined temperature in order to release aerosol from the plurality of particles. The plurality of particles may be held together by a binder which melts, or otherwise loses its binding properties, at a predetermined temperature. The particles may have a known distribution of shapes, sizes and materials such that, within a single bead or pellet, there is statistically consistent and homogeneous distribution of the particles from one pellet to another. As a result, the parameters of the pellet, for example, overall shape, size and surface area, will be consistent from one pellet to another. The plurality of particles may comprise particles of tobacco and an inert material.

There may be different categories of aerosol-generating article, each providing a different user experience. For example, the different categories may comprise articles having different recipes or compositions of aerosol-forming substrates, different concentrations of nicotine or other components and different quantities or thicknesses of aerosol-forming substrate. Aerosol-generating articles belonging to the same category may have the same shape, size or colour to make them identifiable to a user or to an aerosol-generating system or device. An aerosol-generating system or device may be configured to only accept a certain category of aerosol-generating article, for example, by having a delivery aperture or mechanism which only accepts a certain size or shape of article. Alternatively, an aerosol-generating system or device may be configured to determine the category of aerosol-generating article which has been inserted into the system or device, for example, by using a sensor for detecting the shape, size or colour of the article. The aerosol-generating system or device may store a set of heating programs or regimes corresponding to the category of article which has been inserted. Upon detecting the category of article, the aerosol-generating system or device may be configured to execute the heating program or regime corresponding to the type of article which has been inserted.

The flow controller may comprise any suitable device for controlling the flow of air through the airflow pathway. For example, the flow controller may comprise a valve such as a gate valve, an aperture valve, a butterfly valve, a flap valve, a piston valve, a solenoid valve or any other suitable valve. The flow controller may comprise a pair of control members each of which comprising a portion of the airflow pathway. At least one of the members may be translatable or rotatable relative to the other member such that its portion of the airflow pathway can be brought into alignment with the portion of the airflow pathway of the other member when the flow controller is in an open configuration or moved out alignment with the portion of the airflow pathway of the other member when the flow controller is in a closed configuration. The flow controller may be manually operable or electrically operable.

The heating element may comprise an electrically resistive heating element. The heating element may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum platinum, gold and silver. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese-, gold- and iron-containing alloys, and superalloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required.

The heating element may be an inductive heating element. For example, in some embodiments, the heating element may be a heating element which is heatable by being placed within a time-varying electromagnetic field, for example, a high-frequency alternating electromagnetic field. The inductive heating element may comprise a susceptor material. The heating element may be part of the aerosol-generating system. For example, in some embodiments, the aerosolisation chamber may be at least partially lined or coated with a susceptor material. The heating element may be part of the aerosol-generating article. For example, in some embodiments, the aerosol-generating article may comprise an inductive heating element by comprising a susceptor material. The susceptor material may be incorporated into the aerosol-generating articles in any number of ways. For example, in some embodiments, the aerosol-generating article may comprise a core comprising a susceptor material. In some embodiments, the aerosol-forming substrate may comprise susceptor particles, strips, ribbons, shreds, pellets or beads. In some embodiments, the heating element may be part of both the aerosol-generating system and the aerosol-generating article.

The susceptor material may comprise a ferromagnetic material. The susceptor material may comprise a ferrite material. The susceptor material may comprise a metallic material. The susceptor material may comprise at least one of ferritic iron, ferromagnetic steel, stainless steel, and aluminium. Different materials will generate different amounts of heat when positioned within electromagnetic fields having similar values of frequency and field strength. Therefore, the susceptor material may be selected to provide a desired power dissipation within a known electromagnetic field. In some embodiments, the susceptor material may be heated by means of an electromagnetic coil provided by the aerosol-generating system, the magnetic coil arranged around the aerosolisation chamber.

In embodiments in which the susceptor material comprises stainless steel, the susceptor material may, in some embodiments, comprise at least one 400 series stainless steel. Suitable 400 series stainless steels include grade 410, grade 420, and grade 430.

The heating element may be arranged within the aerosolisation chamber. For example, in some embodiments, the heating element may extend into the aerosolisation chamber or be arranged on an internal surface of the aerosolisation chamber. In some embodiments, the heating element may be formed as a track of electrically resistive material on an internal surface of the aerosolisation chamber. In some embodiments, the heating element may comprise an inductive heating element arranged within the aerosolisation chamber which is heated by an electromagnetic coil arranged around the aerosolisation chamber.

The heating element may be arranged outside of the aerosolisation chamber. For example, the heating element may comprise a resistive heating coil arranged around the aerosolisation chamber.

The heating element may form part of the aerosolisation chamber. For example, the heating element may be integrated into the walls of the aerosolisation chamber or the walls of the aerosolisation chamber may comprise an electrically resistive metallic container.

The aerosol-generating system may comprise a plurality of heating elements.

The aerosol-generating system may comprise insulation provided around the aerosolisation chamber. The insulation may comprise vacuum insulation or an aerogel. The insulation may be U-shaped to provide space for the pellet to be inserted and ejected.

According to another aspect of the invention, there is provided an aerosol-generating device for use in the aerosol-generating system described above. The aerosol-generating device may be configured to generate an aerosol from an aerosol-generating article. The aerosol-generating article may comprise a single metered dose of an aerosol-forming substrate. The aerosol-generating device may comprise an airflow pathway arranged between an air inlet and an air outlet. The aerosol-generating device may comprise an aerosolisation chamber arranged at a location along the airflow pathway such that the airflow pathway passes through at least a portion of the aerosolisation chamber. The aerosol-generating device may comprise a flow controller for selectively controlling the flow of air through the airflow pathway. The flow controller may have an open configuration and a closed configuration. The open configuration of the flow controller may be a configuration in which air can flow into and out of the aerosolisation chamber. The closed configuration of the flow controller may be a configuration in which air is substantially prevented or blocked from flowing into and out of the aerosolisation chamber. The aerosolisation chamber may be configured to receive only one aerosol-generating article at a time. The aerosol-generating device may comprise a heating element. The heating element may be arranged to heat the aerosolisation chamber when an aerosol-generating article is received within the aerosolisation chamber. The aerosol-generating device may be configured to heat the aerosolisation chamber containing an aerosol-generating article only when the flow controller is in the closed configuration.

According to an aspect of the invention, there is provided an aerosol-generating device for use in the aerosol-generating system described above, the aerosol-generating device being configured to generate an aerosol from an aerosol-generating article, the aerosol-generating article comprising a single metered-dose of an aerosol-forming substrate, the aerosol-generating device comprising: an airflow pathway arranged between an air inlet and an air outlet; an aerosolisation chamber arranged at a location along the airflow pathway such that the airflow pathway passes through at least a portion of the aerosolisation chamber; and a flow controller for selectively controlling the flow of air through the airflow pathway, the flow controller having an open configuration in which air can flow into and out of the aerosolisation chamber and a closed configuration in which air is substantially prevented or blocked from flowing into and out of the aerosolisation chamber; wherein the aerosolisation chamber is configured to receive only one aerosol-generating article at a time; the aerosol-generating device further comprising a heating element arranged to heat the aerosolisation chamber when an aerosol-generating article is received within the aerosolisation chamber, wherein the aerosol-generating device is configured to heat the aerosolisation chamber containing an aerosol-generating article only when the flow controller is in the closed configuration.

The device may comprise a housing for housing the aerosolisation chamber, a heating element, airflow pathway and flow controller. The housing may comprise a main body portion. The housing may comprise a mouthpiece portion. The air inlet may be arranged at a point along a length of the housing. The air outlet may be arranged at a mouth end of the mouthpiece portion. In this way a user may be able to puff or inhale on an aerosol via the air outlet, which may be formed at or in the mouthpiece portion. The mouthpiece portion may be separable from the main body portion.

The aerosol-generating device may comprise an electrical power source. The aerosol-generating device may comprise control circuitry. The main body portion may comprise the electrical power source. The main body portion may comprise the control circuitry. The control circuitry may be configured to control the supply of power to the heating element from the power source. The control circuitry may comprise a microprocessor. The microprocessor may be a programmable microprocessor, a microcontroller, or an application specific integrated chip (ASIC) or other electronic circuitry capable of providing control. The control circuitry may comprise further electronic components. For example, in some embodiments, the control circuitry may comprise any of: sensors, switches, display elements. Power may be supplied to the heating element for the duration of a puff either continuously or in the form of pulses of electrical current. The power source may be a battery. The battery may be a lithium iron phosphate battery, within the device. As an alternative, the power source may be another form of charge storage device such as a capacitor.

In some embodiments, the device may further comprise a sensor located within, or in proximity to, the aerosolisation chamber for monitoring the temperature of the aerosolisation chamber or heating element. In some embodiments, the control circuitry may monitor the temperature of the heating element. In some embodiments, the control circuitry may monitor the temperature of the heating element by determining the electrical resistance of the heating element, which resistance being related to the temperature of the heating element. The relationship between resistance and temperature may be defined in an algorithm. The relationship between resistance and temperature mat be defined in a look-up table stored in a memory of the control circuitry.

The device may comprise a sensor for detecting a puff. The sensor may comprise a flow detector arranged in a secondary airflow pathway. The secondary airflow pathway may have a smaller cross-section than the airflow pathway flowing through the aerosolisation chamber. The airflow pathway through the aerosolisation chamber may be referred to as the primary airflow pathway. In some embodiments, the sensor may comprise a capacitive sensor. The capacitive sensor may be arranged in the proximity of the mouthpiece of the device. The capacitive sensor may be configured to detect when a user contacts the mouthpiece with their lips.

According to yet another aspect of the invention, there is provided a method of generating an aerosol. The method may be configured to generate the aerosol from an aerosol-generating article comprising an aerosol-forming substrate. The aerosol-generating article may comprise a single metered-dose of an aerosol-forming substrate. The method may comprise providing an airflow pathway between an air inlet and an air outlet. The method may comprise providing an aerosolisation chamber arranged at a location along the airflow pathway such that the airflow pathway passes through at least a portion of the aerosolisation chamber. The method may comprise placing one aerosol-generating article within the aerosolisation chamber. The method may comprise closing the airflow pathway to substantially prevent or block air from flowing into and out of the aerosolisation chamber. The method may comprise heating the aerosolisation chamber containing the aerosol-generating article such that the aerosol-forming substrate is aerosolised whilst the airflow pathway is closed. The method may comprise opening the airflow pathway such that a user can puff on the generated aerosol via the air outlet.

According to an aspect of the invention, there is provided a method of generating an aerosol, wherein the method is configured to generate the aerosol from an aerosol-generating article, the aerosol-generating article comprising a single metered-dose of an aerosol-forming substrate; the method comprising: providing an airflow pathway between an air inlet and an air outlet; providing an aerosolisation chamber arranged at a location along the airflow pathway such that the airflow pathway passes through at least a portion of the aerosolisation chamber; placing one aerosol-generating article within the aerosolisation chamber; closing the airflow pathway to substantially prevent or block air from flowing into and out of the aerosolisation chamber; heating the aerosolisation chamber containing the aerosol-generating article such that the aerosol-generating substrate is aerosolised whilst the airflow pathway is closed; opening the airflow pathway such that a user can puff on the generated aerosol via the air outlet.

The method may comprise raising the temperature within the aerosolisation chamber to a predetermined temperature prior to placing the aerosol-generating article within the aerosolisation chamber. This allows any variability in the starting temperature of the aerosolisation chamber to be reduced when the aerosol-generating article is inserted. Such variability may be caused by performing the method in different ambient temperatures, for example, indoors as opposed to outdoors or global variation in climate. The predetermined temperature may be an aerosolisation temperature. Preferably, the aerosolisation temperature is between 160 and 350° C. inclusive and the temperature to be used may depend on the type of aerosol-forming substrate and a user's taste preferences. The aerosol-generating system or device may be configured so that a user could control the aerosolisation temperature depending on their taste preferences.

In some embodiments, the method comprises raising the temperature within the aerosolisation chamber to a first predetermined temperature. The first predetermined temperature may be a temperature lower than an aerosolisation temperature used to aerosolise the aerosol-forming substrate. The first predetermined temperature may be a temperature higher than a maximum ambient temperature typically encountered. For example, in some embodiments, the first predetermined temperature may be within the range 50° C. to 300° C. In some embodiments, the first predetermined temperature may be within the range 50° C. to 250° C. In some embodiments, the first predetermined temperature may be within the range 50° C. to 200° C. In some embodiments, the first predetermined temperature may be within the range 50° C. to 150° C. In some embodiments, the first predetermined temperature may be within the range 50° C. to 100° C. The method may comprise raising the temperature within the aerosolisation chamber to a second predetermined temperature. The second predetermined temperature may be an aerosolisation temperature for aerosolising the aerosol-forming substrate. The method may comprise raising the aerosolisation chamber to the second predetermined temperature in response to a signal indicative of an event. The event may be insertion of an aerosol-generating article. The event may be a user pressing a button to signal to the device that they wish to start puffing. The event may be the detection of contact between a mouthpiece and the user's mouth. The event may be detection of a puff. The event may be detection of a start of a puff.

In some embodiments, instead of heating the aerosolisation chamber to a predetermined temperature, the method could detect the starting temperature of the aerosolisation chamber, for example, using a temperature sensor and account for any deviation from an ideal starting temperature as part of the heating process. An algorithm to account for such deviations could be stored in a memory, for example, in a microcontroller forming part of the control circuitry.

Features described in relation to one or more aspects may equally be applied to other aspects of the invention. In particular, features described in relation to the aerosol-generating system may be equally applied to the aerosol-generating device or the method of generating an aerosol and vice versa.

Embodiments of the invention will now be described, by way of example only, with reference to the accompanying drawings, in which:

FIG. 8 is a plan view of a blister pack for storing aerosol-generating articles for use in a system or device in accordance with an embodiment of the invention.

FIGS. 9A, 9B and 9C are schematic cross-sectional side views of an injector-type dispenser for storing and delivering aerosol-generating articles for use in a system or device in accordance with an embodiment of the invention in three different stages of operation respectively.

Figure 1:
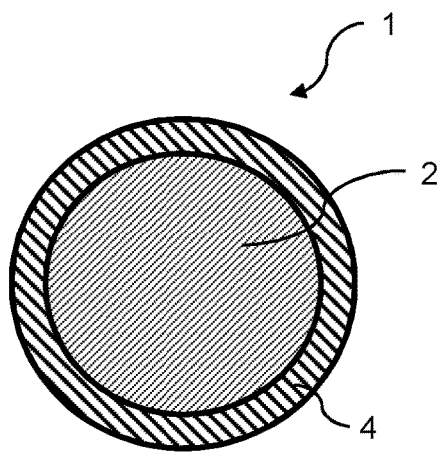
FIG. 1 is a cross-sectional view through an aerosol-generating article for use in a system or device in accordance with an embodiment of the invention.

FIG. 1 shows a cross-sectional view through an aerosol-generating article for use in an aerosol-generating system or device. The aerosol-generating article comprises a substantially spherical or ball-shaped bead or pellet 1 having a core 2 which is coated with an aerosol-forming substrate 4. The core 2 is made from glass which is an inert material and therefore does not produce unwanted by-products when the bead 1 is heated. Glass also has a high melting temperature and therefore is able to withstand the temperatures (generally less than 500° C.) typically encountered during heating without losing its structural integrity. The glass core 2 is also smooth and impermeable or non-porous so that the aerosol-forming substrate 4 is only located on its surface. This makes it easier to accurately control the amount of aerosol-forming substrate 4 being deposited on the surface of the core 2 and reduces variability between beads.

Being substantially spherical, the bead 1 has a central symmetry which results in a repeatable amount of aerosol being generated regardless of the bead's position in an aerosolisation chamber. A spherical shape also permits movement within the aerosolisation chamber. Furthermore, an impermeable or non-porous core means that air can only flow around the outside of the bead 1 rather than through it. This helps to reduce variability in the amount of generated aerosol caused by, for example, the air carrying the aerosol leaving a portion of the aerosol inside the pellet or condensation of the aerosol in cooler internal parts of the bead 1.

Other suitable materials for the core 2 could be used, for example, a ceramic or a thermosetting plastic. For aerosol-generating articles which are intended to be inductively heated, the core 2 could comprise a susceptor material, such as stainless steel.

The bead 1 is a single-use aerosol-generating article and comprises a metered-dose of aerosol-forming substrate 4. The metered-dose constitutes an amount of aerosol-forming substrate 4 sufficient for generating an amount of aerosol for only a single puff or inhalation. The aerosol-forming substrate 4 comprises 100 μg of nicotine, which has been found to be an amount of nicotine suitable for only a single puff. During a typical session, a user may take 10 to 12 puffs on an aerosol-generating device and therefore will use 10 to 12 beads 1 and receive approximately 1.0 to 1.2 mg of nicotine. However, a user does not need to use each of the 10 to 12 beads during a single session but can simply take puffs as and when desired to take a metered-dose. In the described embodiment, the aerosol-forming substrate 4 comprises: 20% to 47% cellulose (dry weight basis); 8% carboxymethyl cellulose; 3% fibre; 35% glycerine and 2% nicotine lactate.

The aerosol-forming substrate 4 is formed as a slurry and coated around the glass core 2 before being cured. The bead 1 is approximately 5 mm in overall diameter with the core 2 having a diameter of around 3 to 3.5 mm and the aerosol-forming substrate 4 having a thickness of approximately 0.75 to 1 mm.

Figure 2:
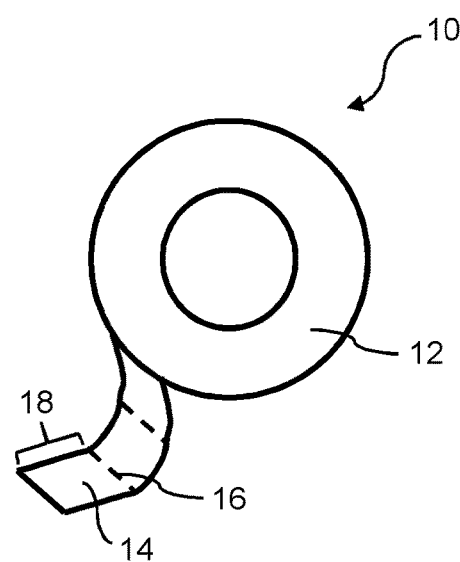
FIG. 2 is a side perspective view of another aerosol-generating article for use in a system or device in accordance with an embodiment of the invention.

FIG. 2 shows a side perspective view of another aerosol-generating article 10 for use in an aerosol-generating system or device. The aerosol-generating article 10 comprises a length of paper strip 14 which is spooled on to a reel 12. The paper strip 14 acts as an absorbent carrier material which is impregnated with a liquid or gel aerosol-forming substrate (not shown). The paper strip 14 is provided with a series of markings or perforations 16 across its width at regularly spaced apart intervals to define a series of paper sections 18. Each paper section 18 contains an amount of aerosol-forming substrate sufficient for generating an amount of aerosol for only a single puff. In use, a user can tear off one paper section 18 at the next set of markings or perforations 16 and insert the paper section 18 into an aerosol-generating device or system to generate an aerosol for a single puff. The aerosol-forming substrate comprises a nicotine salt and an aerosol-former. The reel 12 comprises a cover (not shown) for covering the reel 12 when not in use to prevent evaporation or degradation of the aerosol-forming substrate.

Figure 3:
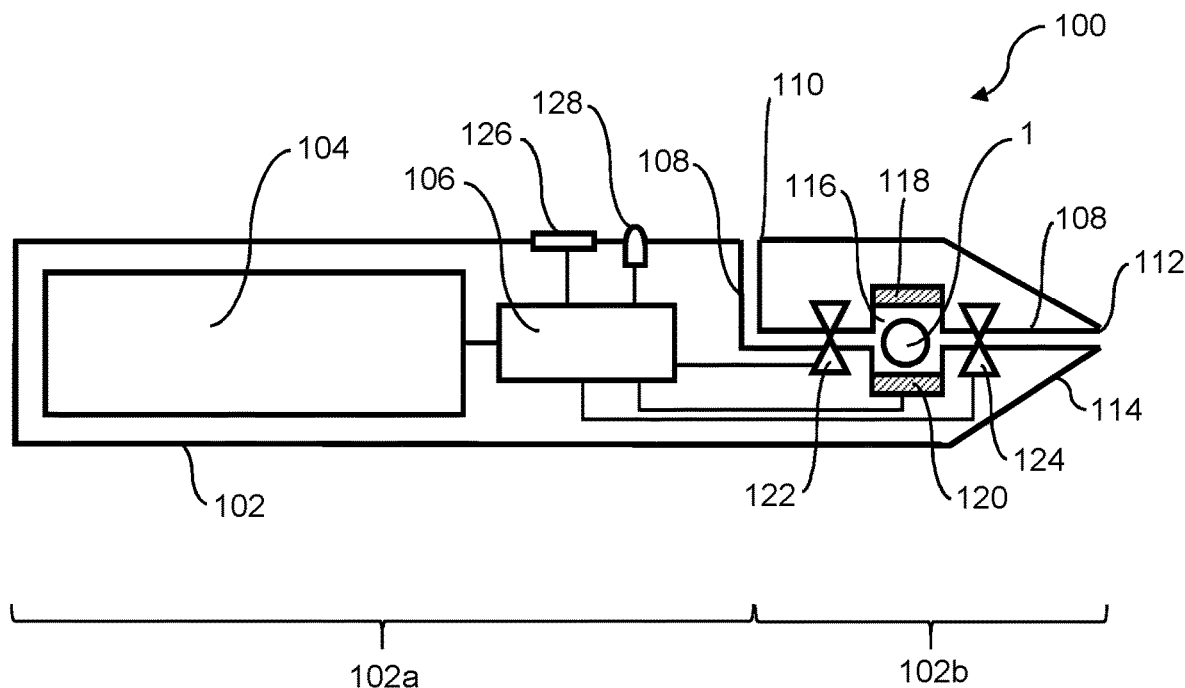
FIG. 3 is a schematic cross-sectional side view of a device in accordance with an embodiment of the invention.

FIG. 3 shows a schematic cross-sectional side view of an aerosol-generating device 100 comprising a housing 102 having a main body portion 102*a* and a mouthpiece portion 102*b*. The main body portion 102*a* comprises a battery 104, which acts a power source, and control circuitry 106 for controlling the operation of the device 100. The mouthpiece portion 102*b* comprises an air inlet 110 arranged in an upper part of the housing 102 and an air outlet 112 arranged in a mouthpiece 114 at a mouth-end of the mouthpiece portion 102*b*. An airflow pathway 108 is arranged between the air inlet 110 and the air outlet 112. The airflow pathway is in the form a conduit or passage which passes through the mouthpiece portion 102*b*. An aerosolisation chamber 116 is arranged at a location along the airflow pathway 108. At least a portion of the airflow pathway 108 passes through the aerosolisation chamber 116. In other words, the aerosolisation chamber 116 is part of the airflow pathway 108.

In the described embodiment, a first heating element 118 is arranged in an upper part of the aerosolisation chamber 116 and a second heating element 120 is arranged in a lower part of the aerosolisation chamber 116. However, in some embodiments, the aerosolisation chamber could be heated by a single heating element which lines the walls of the aerosolisation chamber. The heating elements 118 and 120 are resistive heating elements and are electrically connected to the battery 104 via the control circuitry 106. The heating elements 118 and 120 are arranged to heat an aerosol-generating article located within the aerosolisation chamber 116. The aerosolisation chamber 116 has an aperture or opening (not shown) so that the aerosolisation chamber can receive an aerosol-generating article. The opening can be closed to contain the aerosol-generating article. FIG. 3 shows a bead 1, such as that illustrated in FIG. 1, located within the aerosolisation chamber. The aerosolisation chamber 116 also comprises a temperature sensor (not shown) for determining the temperature within the aerosolisation chamber 116.

The aerosol-generating device 100 further comprises a first valve 122 arranged at a point along the airflow pathway 108 upstream of the aerosolisation chamber 116 and a second valve 124 arranged at a point along the airflow pathway 108 downstream of the aerosolisation chamber 116. The valves 122 and 124 are electrically operated and are connected to and can be controlled by the control circuitry 106. The valves 122 and 124 act as a flow controller for selectively controlling the flow of air through the airflow pathway 108, in particular through the aerosolisation chamber 116. When valves 122 and 124 are open, air can flow into and out of the aerosolisation chamber 116 and when valves 122 and 124 are closed air is substantially blocked from flowing into and out of the aerosolisation chamber 116. The valves 122 and 124 are therefore able to isolate the aerosolisation chamber 116 such that the bead 1 can be heated in a closed system, that is aerosol is inhibited from leaking out of the aerosolisation chamber 116 when the valves 122 and 124 are closed.

A switch 126 is provided to enable a user to indicate to the device 100 when they wish to take a puff. The switch 126 is arranged on an outer upper surface of the housing 102 and is connected to the controlled circuitry 106. When the switch 126 is depressed, a signal is sent to the control circuitry 106 that the user wishes to take a puff. An indicator in the form of light emitting diode (LED) 128 is provided on an outer upper surface of the housing 102 to indicate to a user when aerosol has been generated in the aerosolisation chamber 116 and the device 100 is ready for a puff to be taken.

Figure 4A:
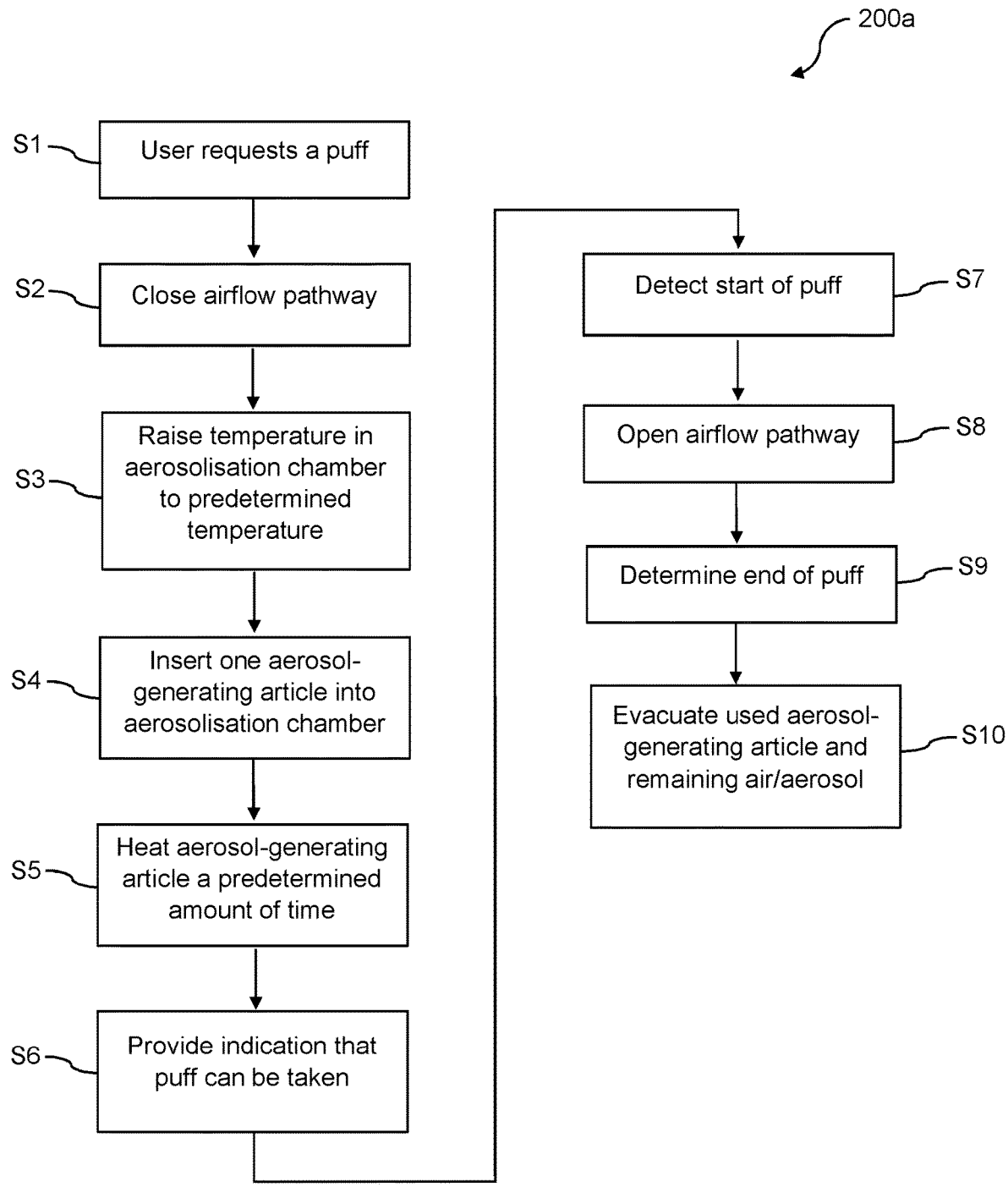
FIG. 4A is a flow chart showing a method of generating an aerosol in accordance with an embodiment of the invention.

FIG. 4A shows a flow chart setting out a method 200*a* of generating an aerosol from a single use aerosol-generating article as described herein and in which the aerosol-generating article comprises a predetermined amount of an aerosol-forming substrate. The method may be performed by an aerosol-generating system or device as described herein.

The method starts at step S1, where a user requests a puff. A puff may be requested on demand, for example:

by a user pressing a switch; or by a user activating a mechanism to deliver a pellet into the aerosolisation chamber; or by detecting a user placing a mouthpiece of the device to their lips, e.g. by using a capacitive sensor located in the mouthpiece; or by puff detection, i.e. using a flow sensor to detect a user puffing on the device.

Alternatively, the puff may be requested as part of a planned program, for example, as part of a medical program. In which case, when the scheduled time for a puff is reached, the method may indicate to the user, for example, using a visual or audible alert, and the user can decide whether to validate (or not) the start of the process, for example, by pressing a switch. In the device 100 of FIG. 3, a puff is requested by pressing switch 126.

The next step S2 is to close the airflow pathway. This substantially blocks air from flowing into and out of the aerosolisation chamber so that aerosol can be generated within the aerosolisation chamber to retain the aerosol until the user takes a puff. In the device 100 of FIG. 3, this is achieved by closing valves 122 and 124.

The next step S3 is to raise the temperature in the aerosolisation chamber to a predetermined temperature. In this embodiment, the predetermined temperature is the aerosolisation temperature required to aerosolise the aerosol-forming substrate. Preheating the aerosolisation chamber to the aerosolisation temperature allows any variability in the starting temperature of the aerosolisation chamber to be reduced when the aerosol-generating article is inserted. The aerosolisation temperature depends on the type of aerosol-forming substrate being used and also a user's taste preferences and in this embodiment is between 160 and 350° C. inclusive. An aerosol-generating system or device will know that type of aerosol-generating article it has to heat, either because it is adapted to heat a certain type of article or it will be able to determine the type of article which has been inserted into the aerosolisation chamber based on attributes of the article, such as its shape or colour or because a user has input such information, for example, via a user interface (not shown). It will therefore know the type of aerosol-forming substrate comprised in the article, the thickness of the aerosol-forming substrate on the core 2 or a carrier material and the geometry of the aerosol-generating article. The device can therefore determine to what aerosolisation temperature the device is required to heat the aerosol-generating article. Alternatively, a user can control the aerosolisation temperature via a user interface according to their taste preferences.

In the device 100 of FIG. 3, the temperature sensor (not shown) located within the aerosolisation chamber 116 sends a signal to the control circuitry 106 that the aerosolisation chamber 116 has reached the aerosolisation temperature. The LED 128 may indicate that the aerosolisation chamber 116 has reached the aerosolisation temperature, for example, by flashing or displaying a certain colour. Once the aerosolisation chamber 116 has reached the aerosolisation temperature, it is ready to receive an aerosol-generating article such as bead 1 illustrated in FIG. 1. The device may prevent a bead from being inserted into the aerosolisation chamber until the aerosolisation temperature has been reached.

Step S3 is not essential to the method 200*a* of generating an aerosol. Instead of heating the aerosolisation chamber to a predetermined temperature, the method could detect the starting temperature of the aerosolisation chamber, for example, using the temperature sensor of the device 100 of FIG. 1, and account for any deviation from an ideal starting temperature as part of the heating process, i.e. in step S5 discussed below. An algorithm to account for such deviations could be stored in a memory, for example, in a microcontroller forming part of the control circuitry 106 of the device 100 of FIG. 1.

The next step S4 is to insert one aerosol-generating article into the aerosolisation chamber. Only one aerosol-generating article is inserted at a time and there is only one article in the aerosolisation chamber at any one time to deliver a single metered-dose. Therefore, an article is inserted into the aerosolisation chamber only after, or at the same time as, the previous expended article is evacuated from the aerosolisation chamber. A number of ways of inserting the aerosol-generating article are discussed below.

The next step S5 is to heat the aerosol-generating article for a predetermined amount of time in order to generate an aerosol. The aerosolisation temperature is already at the aerosolisation temperature. An aerosol-generating device will know that type of aerosol-generating article it has to heat, either because it is adapted to heat a certain type of article or it will be able to determine the type of article which has been inserted into the aerosolisation chamber based on attributes of the article, such as its shape or colour or because a user has input such information, for example, via a user interface (not shown). It will therefore know the type of aerosol-forming substrate comprised in the article, the thickness of the aerosol-forming substrate on the core 2 or a carrier material and the geometry of the aerosol-generating article. The device can therefore determine how long to heat the aerosol-generating article at the aerosolisation temperature to aerosolise the aerosol-forming substrate. Again, a heating algorithm or a look-up table containing heating parameters can be stored in a memory, for example, in a microcontroller forming part of the control circuitry 106 of the device 100 of FIG. 1. The aerosol-generating article is heated such that substantially all the aerosol-forming substrate is aerosolised and so that a user knows how much aerosol and aerosol components they are receiving. Once all the aerosol-forming substrate has been aerosolised, the method has reached a point at which a puff can be taken.

The next step S6 is to provide an indication that a puff can be taken. By indicating to a user when they can take a puff, variability in the amount of aerosol deliverable to the user may be reduced because a user is prevented from taking a puff whilst the aerosol is still being generated. Indication can be provided by sending a visual or audible signal to the user or via some other signal, for example, haptic feedback. In the device 100 of FIG. 3, the indication is provided by the LED 128, for example, by changing from a flashing state to a continuous state or by changing colour, for example, from amber to green.

The next step S7 is to detect the start of the puff. The start of the puff could be detected in a number of different ways, for example:

- by detecting a switch being pressed following the indication being provided that a puff can be taken; or
- by providing a secondary airflow pathway, having a smaller cross-sectional area so as to not disturb the primary airflow pathway flowing through the aerosolisation chamber, and using a flow sensor or puff sensor to detect a flow of air through the secondary airflow pathway caused by a user taking a puff; or
- by detecting a user placing a mouthpiece of the device to their lips, e.g. by using a capacitive sensor located in the mouthpiece.

In the device 100 of FIG. 3, the start of the puff is detected by a user pressing switch 126 following the indication being provided that a puff can be taken.

The next step S8 is to open the airflow pathway so that the generated aerosol can leave the aerosolisation chamber and a user can puff on the aerosol. In the device 100 of FIG. 3, this is achieved by opening the valves 122 and 124.

The next step S9 is to determine the end of the puff. The end of a puff can be determined by, for example:

- by allowing a certain amount of elapsed time since the start of the puff for the puff to be completed; or
- by detecting a loss of a puff sensor signal at a time T1 during a predetermined time period T, which puff sensor signal was activated at the start of the puff, e.g. if T1<T then this would indicate that the user interrupted a puff before it was finished and therefore did not receive the full amount of aerosol but if T1>T then this would indicate that the puff was completed and the method can reset for a new puff; or
- by detecting removal of a user's lips from the mouthpiece of device, for example, using a capacitive sensor; or
- a combination of the above.

A puff sensor for detecting the end of a puff can be placed on the primary airflow pathway, i.e. the pathway flowing through the aerosolisation chamber, because this will be open whilst the puff is being taken. The puff sensor could monitor the flow of air drawn through the airflow pathway during a puff and any variation can be evaluated to determine whether the quantity of air drawn through the aerosolisation chamber during a puff was sufficient to take all the aerosol in the aerosolisation chamber. The amount of aerosol generated and any variation in the amount of aerosol taken can be stored in a memory, for example, in a memory of a microcontroller forming part of the control circuitry 106 of the device 100 of FIG. 3, and provide information about the amount of aerosol and aerosol components received by a user. The final step S10 in the method 200*a* is to evacuate the used aerosol-generating article and any remaining air or aerosol in the aerosolisation chamber. This could be achieved by, for example:

- by providing an evacuation mechanism such as a piston for pushing the aerosol-generating article out of the device or system or toward a reservoir of used articles. This would also evacuate any remaining aerosol in the aerosolisation chamber; or
- by making the evacuation of the aerosol-generating article part of the step of inserting a new article such that the evacuation is carried out automatically, e.g. the mechanism for inserting a new article could simultaneously evacuate a used article from the aerosolisation chamber as well as expel any remaining aerosol.

Any remaining aerosol in the aerosolisation chamber could be expelled via the main airflow pathway or via a dedicated evacuation pathway. Any aerosol remaining in the aerosolisation chamber following a puff will cool and condense or its properties otherwise change undesirably. Therefore having a dedicated evacuation pathway could be useful to prevent the remaining aerosol contaminating the main airflow pathway.

Figure 4B:
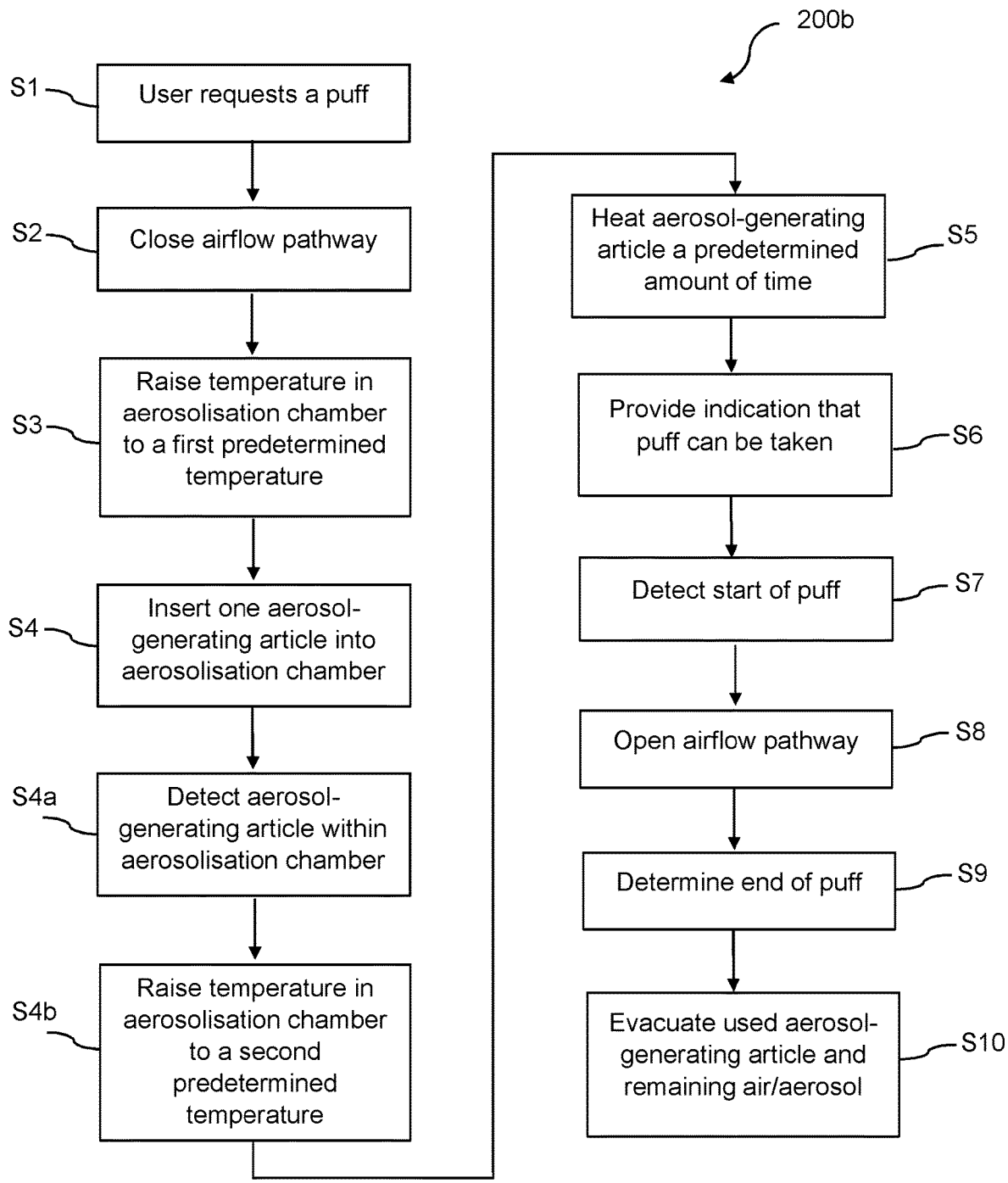
FIG. 4B is a flow chart showing a method of generating an aerosol in accordance with another embodiment of the invention.

FIG. 4B shows a flow chart setting out another method 200*b* of generating an aerosol from a single use aerosol-generating article as described herein and in which the aerosol-generating article comprises a predetermined amount of an aerosol-forming substrate. Again, the method may be performed by an aerosol-generating system or device as described herein.

In FIG. 4B, method steps S1, S2, S4 and S5 to S10 of method 200*b* are identical to the corresponding method steps set out in method 200*a* of FIG. 4A.

Method step S3 of method 200*b* involves raising the temperature in the aerosolisation chamber to a first predetermined temperature. The first predetermined temperature is lower than an aerosolisation temperature used to aerosolise the aerosol-forming substrate. The first predetermined temperature is higher than a maximum ambient temperature typically encountered. The predetermined temperature in the described embodiment is approximately 90° C., although this can be varied as required. The first predetermined temperature is also generally higher than the temperature the aerosolisation chamber or heating elements reduce to following a heating cycle when they are not being supplied with power, i.e. due to heat loss between puffs. This allows any variability in the starting temperature of the aerosolisation chamber to be reduced when the aerosol-generating article is inserted. In the device 100 of FIG. 3, the temperature sensor (not shown) located within the aerosolisation chamber 116 sends a signal to the control circuitry 106 that the aerosolisation chamber 116 has reached the first predetermined temperature. The LED 128 may indicate that the aerosolisation chamber 116 has reached the first predetermined temperature, for example, by flashing or displaying a certain colour. Once the aerosolisation chamber 116 has reached the predetermined temperature, it is ready to receive an aerosol-generating article such as bead 1 illustrated in FIG. 1. The device may prevent a bead from being inserted into the aerosolisation chamber until the first predetermined temperature is reached.

In step S4 of method 200*b* an aerosol-generating article is inserted into the aerosolisation chamber in the same way as in method 200*a*.

Method 200*b* of FIG. 4B then comprises an additional step compared to method 200*a* of FIG. 4A, that is step S4*a* which involves detecting the aerosol-generating article within the aerosolisation chamber. This may be done with a sensor, for example, a light sensor or micro-switch which is triggered as the aerosol-generating article is inserted.

Method 200*b* of FIG. 4B then comprises a further additional step S4*b* of raising the temperature within the aerosolisation chamber to a second predetermined temperature. The second predetermined temperature is the aerosolisation temperature required to aerosolise the aerosol-forming substrate. The determination of the aerosolisation temperature in method 200*b* is the same as for method 200*a*.

Figure 5:
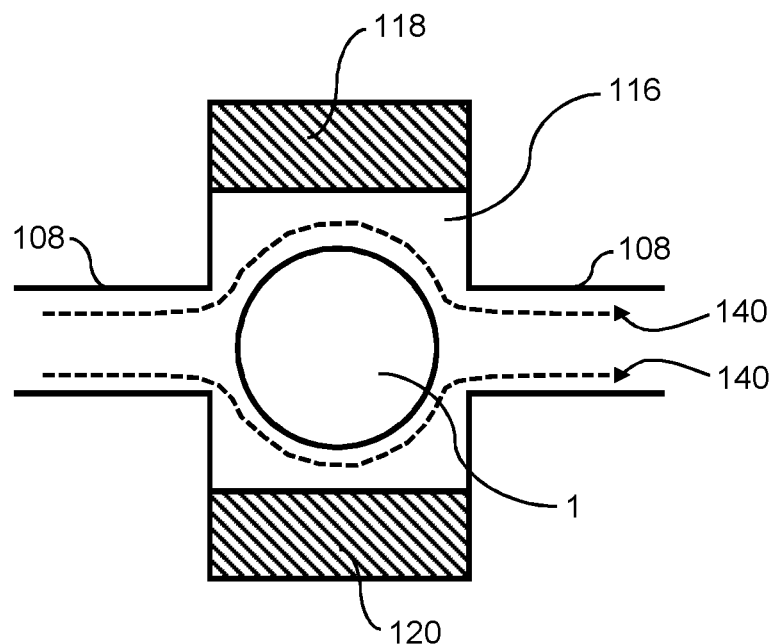
FIG. 5 is an enlarged cross-sectional side view of the aerosolisation chamber of the device of FIG. 3 showing the airflow around an aerosol-generating article located within the aerosolisation chamber.

FIG. 5 is an enlarged cross-sectional side view of the aerosolisation chamber 116 of the device 100 of FIG. 3. As in FIG. 3, an aerosol-generating article in the form the substantially spherical bead 1 of FIG. 1 is located in the aerosolisation chamber 116 between upper and lower heating elements 118 and 120. The aerosolisation chamber 116 is sized to received only one bead 1. Airflow pathway 108 enters the aerosolisation chamber 116 at the left of FIG. 5 and exits at the aerosolisation chamber 116 at the right of FIG. 5. The cross-sectional area of the bead 1 in a plane perpendicular to the direction of airflow through airflow pathway 108 is less than the cross-sectional area of the aerosolisation chamber 116 such that air can flow around the bead 1 and through the aerosolisation chamber 116. The smaller cross-sectional area of the bead 1 also allows the bead 1 to move with the aerosolisation chamber 116. Dashed arrows 140 in FIG. 5 schematically show an example airflow through the airflow pathway 108 and aerosolisation chamber 116. Upon entering the aerosolisation chamber 116 via the airflow pathway, the airflow is diverted around the bead 1 before exiting the aerosolisation chamber 116 via the airflow pathway 108 along substantially the same line as it entered. The flow of air around the bead 1 causes the bead to move with the aerosolisation chamber 116. This creates a rattling sound which provides an audible indication to a user that air is flowing through the aerosolisation chamber. The movement of the bead 1 within the aerosolisation chamber 116 also helps to entrain the generated aerosol within the airflow 140.

As shown in FIG. 5, the cross-sectional area of the airflow pathway 108 in a plane perpendicular to the direction of airflow through airflow pathway 108 is less than the cross-sectional area of the bead 1. The height or diameter of the airflow pathway 108 is less than the diameter of the bead 1 and the diameter of the core 2 of the bead 1. The reduced diameter of the airflow pathway 108 therefore acts as a guard which prevents the bead 1 from leaving the aerosolisation chamber 1 via the airflow pathway 108 both in the preheated and post-heated states of the bead 1. The bead 1 and core 2 simply will not fit into the airflow pathway 108. However, other forms of suitable guard may be used, for example, a physical member, such as a mesh, may be placed across at least a portion of the entrance and exit of the airflow pathway 108.

Figure 6:
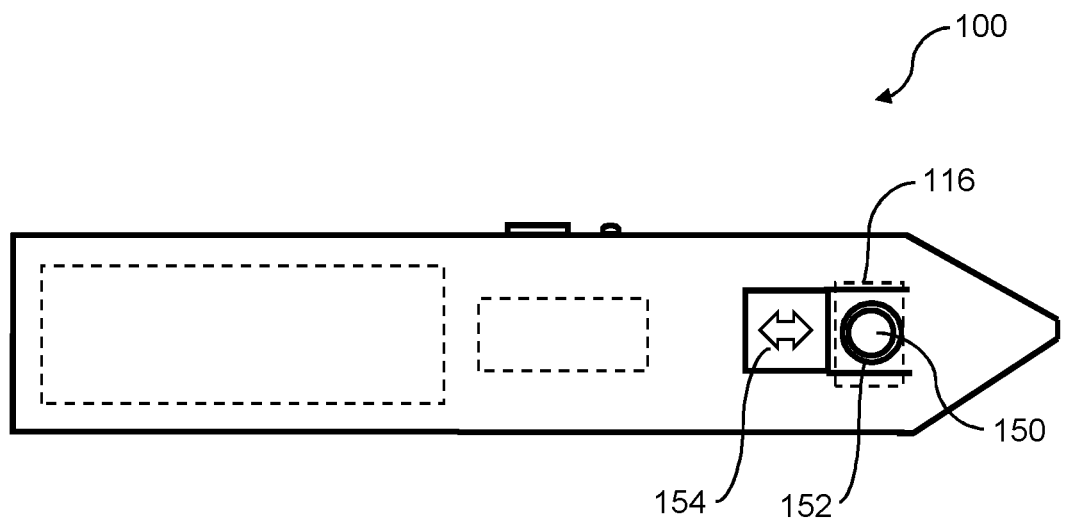
FIG. 6 is a schematic side view of the device of FIG. 3 showing an aperture for delivering an aerosol-generating article into the aerosolisation chamber.

FIG. 6 shows a schematic side view of the device 100 of FIG. 3. The device 100 comprises an aperture 150 for delivering an aerosol-generating article into the aerosolisation chamber 116. The aperture 150 defines the opening of a conduit (not shown) which passes from aperture 150 to a similar aperture (not shown) in a side wall of the aerosolisation chamber 116. The conduit allows communication between an exterior of the device 100 and the interior of the aerosolisation chamber 116 so that an aerosol-generating article can be inserted into the aerosolisation chamber 116. The aperture 150 is circumscribed by a recessed rim 152 which is adapted to engage the end of an insertion device, such as the insertion pen shown in FIGS. 9A to 9C. The aperture 150 is closed by a slidable closure 154 which can move back and forth, as denoted by the double ended arrow in FIG. 6, between a closed position in which it closes aperture 150 and an open position in which the aperture 150 is available for inserting an aerosol-generating article. The closure 154 is biased towards the closed position by a spring (not shown). A similar aperture and closure (not shown) is provided on the opposing side of the device for allowing an aerosol-generating article to be removed from the aerosolisation chamber 116. When aerosol-generating article such as the bead 1 illustrated in FIG. 1 is inserted through aperture 150, a used bead already in the aerosolisation chamber 116 would be pushed out of the opposing aperture such that only one bead can be present within the aerosolisation chamber 116 at any one time.

Figure 7A:
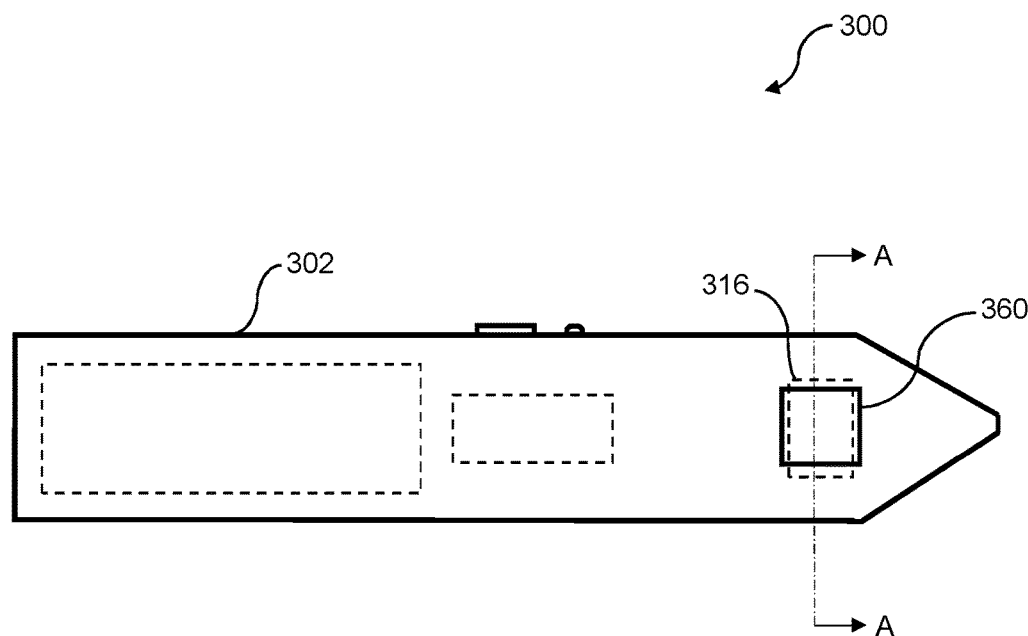
FIG. 7A is a schematic side view of a device in accordance with another embodiment of the invention having a drawer mechanism for delivering an aerosol-generating article into the aerosolisation chamber of the device.

FIG. 7A shows a schematic side view of a device 300 in accordance with another embodiment of the invention. The features and principle of operation of the device 300 of FIG. 7A are the same as that of the device 100 of FIG. 3 with the exception that the device 300 has a drawer mechanism 360, which can extend from the housing 302 of the device 300 for delivering an aerosol-generating article into the aerosolisation chamber 316.

Figure 7B:
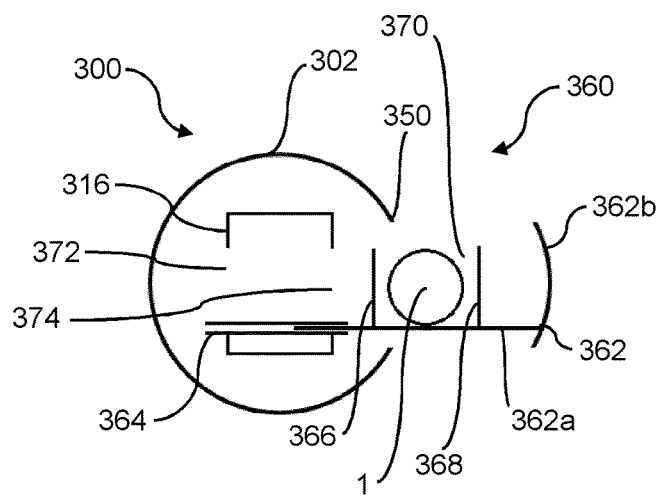
FIGS. 7B and 7C are schematic cross-sectional views taken along the line A-A in FIG. 7A showing the drawer mechanism in an open and closed configuration respectively.
Figure 7C:
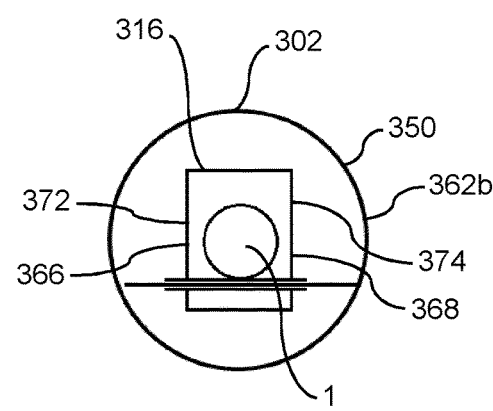

FIGS. 7B and 7C are enlarged schematic cross-sectional views taken along the line A-A in FIG. 7A and show the drawer mechanism 360 in greater detail. FIG. 7B shows the drawer mechanism 360 in an open configuration. The drawer mechanism 360 comprises a drawer 362 having a base 362*a* and a drawer wall 362*b* extending substantially transversely to the base 362*a* at an outer end of the drawer 362. The drawer wall 362*b* forms part of the housing 302 of the device 300 and conforms to the curved shape of the housing 302. The drawer wall 362*b* closes an aperture 350 formed in the side of the housing 302 when the drawer mechanism 360 is in the closed configuration (see FIG. 7C). The drawer base 362*a* slidably engages a pair of rails 364 located on each side of the aerosolisation chamber 316 so that the drawer 362 can slide into and out of the device 300. First 366 and second 368 uprights extend from the drawer base 362*a* and define between them a receiving zone 370 for receiving an aerosol-generating article. FIG. 7B shows a bead 1 as illustrated in FIG. 1 received in the receiving zone 370. The first 366 and second 368 uprights form part of the side walls of the aerosolisation chamber 316 and respectively close openings 372 and 374 formed in the side walls of the aerosolisation chamber 316 when the drawing mechanism 360 is in the closed configuration (see FIG. 7C) to prevent aerosol escaping from the aerosolisation chamber 316 during heating. The uprights 366 and 368 are joined by a pair of side walls (not shown) to define the lateral edges of the receiving zone and to prevent the bead 1 from rolling out from between the uprights 366, 368 when the drawer is in the open configuration. The side walls of the receiving zone 370 are inset from the sides of the drawer base 362*a* which engages the rails 364 to prevent them from interfering with the rails when the drawer 362 slides into the device 300.

FIG. 7C shows the drawer mechanism 360 in the closed configuration. In the closed configuration, drawer wall 362*b* closes aperture 350 formed in housing 302 of the device 300 and uprights 366 and 368 respectively close apertures 372 and 374 formed in the side walls of the aerosolisation chamber 316. An aerosol-generating bead 1 is located within the aerosolisation chamber 316 and can be heated. Once the bead 1 has been heated the drawer mechanism 360 can be returned to the open configuration to remove the used bead 1. The drawer 362 has a push to open/push to close spring latch mechanism (not shown). A user can open the drawer 362 by pushing the drawer wall 362*b* inwardly a small distance to release the latch cause the drawer to spring open under the action of the spring. The drawer 362 can be closed by pushing the drawer wall 362 a small distance inward of the housing 302 to reengage the latch such that the drawer 362 is retained in the closed configuration under the action of the spring.

FIG. 8 is a plan view of a blister pack 400 for storing a plurality of aerosol-generating articles for use in an aerosol-generating system or device. The blister pack 400 acts a storage unit for the articles. The blister pack 400 comprises a polymer layer 478 having a plurality of blisters or pockets 480 extending from a first surface 478*a* of the polymer layer 478. The blisters 480 can be used for storing aerosol-generating articles (not shown). A second opposing surface (not shown) of the polymer layer 478 is covered by a frangible laminate layer (not shown) which is hermetically sealed to the second surface to seal the articles with the blisters 480. In use, a user manually removes an aerosol-generating article from the blister pack 400 by rupturing the frangible laminate layer and then manually inserts the article into an aerosol-generating device, for example, via the aperture 150 of device 100 of FIG. 1 or via the drawer mechanism 360 of the device 300 of FIGS. 7A to 7C.

FIGS. 9A, 9B and 9C show schematic cross-sectional side views of an injector-type dispenser 500 or pen for storing and delivering aerosol-generating articles for use in an aerosol-generating system or with a device. The figures respectively show the dispenser 500 in three different stages of operation respectively.

The dispenser comprises a housing 582 containing a rod 583, a carriage 584 and two springs 585. Within the housing 582 there is a first storage zone 586 for storing a plurality of aerosol-generating beads 1 in axial alignment. In the embodiment shown in FIGS. 9A to 9C, the dispenser 500 also comprises within the housing 582 a second storage zone 587 also for storing a plurality of aerosol-generating beads 1 in axial alignment. The dispenser 500 comprises an exit orifice 588 at a lower dispensing end of the housing 582. The exit orifice 588 is circumscribed by a protruding rim 594 which is adapted to engage an aperture, or in particular a recessed aperture rim, of an aerosol-generating device, for example, the aperture 150 or recess rim 152 of device 100 of FIG. 6. The dispenser 500 further comprises a loading zone 589 disposed between the two storage zones 586 and 587 and the exit orifice 588. The loading zone 589 is sized to accommodate a single aerosol-generating bead 1. The dispenser 500 further comprises first 591 and second 592 hard stops located at either side of a lower end of the loading zone 589.

The springs bias the carriage 584 towards the aerosol-generating beads 1 stored in the first 586 and 587 storage zones. The carriage 584 further comprises a first end face 595 and a second end face 597 which define the rear end of the first 586 and second 587 storage zones respectively. The first end face 595 is set further forwards, i.e. further towards the exit orifice 588, than the second end face 597. The distance in the longitudinal direction between the first 595 and the second 597 end faces is half the diameter of a single aerosol-generating bead 1.

The rod 583 can reciprocate along and through the central longitudinal axis of the housing 582 and through a central longitudinally extending passage 593 formed through the carriage 584. At its dispensing end, the rod 583 has an engagement face 596 for engaging an aerosol-generating bead 1, which engagement face 596 protrudes laterally such that it is wider than the main stem of the rod 583. The rod 583 is actuated by a button 590 located at an actuation end of the rod 583, i.e. at the end opposite to the engagement face 596. Either side of the rod 583 has a toothed section (not shown) which engages a respective rod engagement mechanism formed on each of the corresponding inside surfaces of the passage 593. The inner surface of the housing 582 also has a toothed section facing either side of the carriage 584 which engages a respective housing engagement mechanism on either side of the carriage 584.

In FIG. 9A, each storage zone 586 and 587 contains four axially aligned aerosol-generating beads 1 and the loading zone 589 contains a single aerosol-generating bead 1. At the stage shown in FIG. 9A, the button 590 has started to be depressed and the rod 583 has begun to advance towards the exit orifice 588. At this stage, the rod engagement mechanism of the carriage 584 engages with the toothed sections of the rod 583. As a result, the carriage 584 also advances towards the exit orifice 588. As it advances, the cartridge 584 pushes the rows of axially aligned aerosol-generating beads 1 in both the first and second storage zones 586 and 587 towards the exit orifice 588.

In FIG. 9B, the carriage 584 is no longer able to advance as the aerosol-generating beads 1 in the first storage zone 586 are pushed against the first hard stop 591 by the first end face 595 of the carriage 584. At this point, the rod engagement mechanism disengaged and the rod 583 continued to advance independently of the carriage 584 has pushed the aerosol-generating bead 1, which was disposed in the loading zone 589 in FIG. 9A, through the exit orifice 588. The dispensing end of the rod 583 has passed though the exit orifice 588 and continues to push the aerosol-generating bead 1 until the rod reaches the fully extended position. At this point the aerosol-generating bead 1 would be within the aerosolisation chamber of an aerosol-generating device.

In FIG. 9C the rod 583 has been moved back to the fully retracted position. The housing engagement mechanism of the carriage 584 prevents the carriage 584 moving rearwards with the rod 583. As the engagement face 596 of the rod 583 passed the first 586 and second 587 storage zones, the protrusions at the engagement face 596 pushed the row of aligned aerosol-generating beads 1 in the second storage zone 587 rearwards towards the second end face 597 of the carriage 584. The protrusions at the engagement face 596 of the rod 583 also acted on the row of aligned aerosol-generating beads 1 in the first storage zone 586, however, since the first end face 595 of the carriage 584 is set further forwards than the second end face 597 of the carriage 584, there is no space into which the aerosol-generating beads 1 may move. As a result, the engagement face 596 of the rod 583 moved rearwards into the first storage zone 586 while the aerosol-generating beads 1 remain in place such that the engagement face 596 of the rod 583 moved rearward past the furthest forward aerosol-generating bead 1 in the first storage zone 586, which falls into the loading zone 589. There are now four axially aligned the aerosol-generating beads 1 in the second storage zone 587, three axially aligned the aerosol-generating beads 1 in the first storage zone 586 and the single the aerosol-generating bead 1 in the loading zone 589 is ready to be dispensed.

Figure 10:
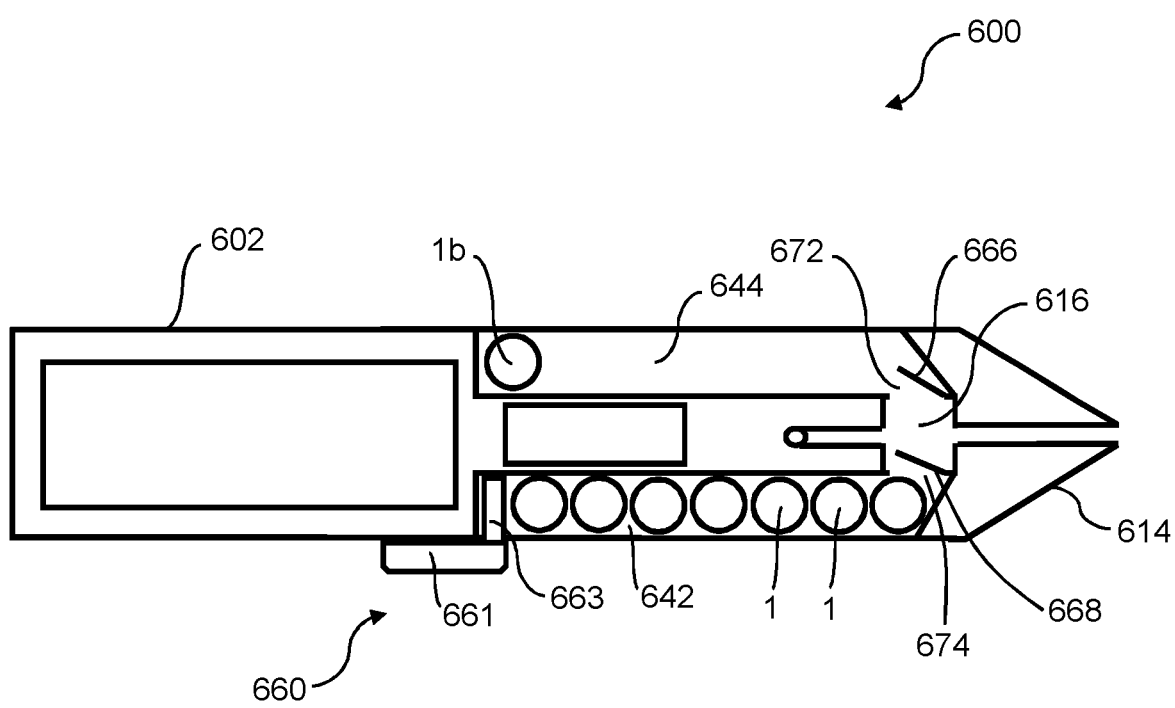
FIG. 10 is a plan cross-sectional view of a device in accordance with a further embodiment of the invention having an integral store and delivery mechanism for respectively storing a plurality of aerosol-generating articles and delivering an aerosol-generating article to an aerosolisation chamber of the device.

FIG. 10 shows a plan cross-sectional view of a device 600 in accordance with a further embodiment of the invention. The features and principle of operation of the device 600 of FIG. 10 are the same as that of the devices 100 and 300 of FIGS. 3 and 7A respectively with the exception that the device 600 has an integral first reservoir 642 and a delivery mechanism 660 for respectively storing a plurality of aerosol-generating beads 1 and delivering an aerosol-generating bead 1 to the aerosolisation chamber 616 of the device 600. The device 600 also has an integral second reservoir 644 for storing used aerosol-generating beads 1b which have been ejected from the aerosolisation chamber 616.

The first reservoir 642 is located within the housing 602 of the device 600 and extends longitudinally along one side of the device 600. The delivery mechanism 660 includes a slider 661 which is slidably engaged in a longitudinal groove (not shown) formed in the housing 602, which groove extends the length of the first reservoir 642. The slider 661 has a pusher part 663 which extends into the first reservoir 642 via the longitudinal groove and is arranged to engage the rearmost aerosol-generating bead 1 stored in the first reservoir 642. The portion of the pusher part 663 which extends into the first reservoir 642 is wider than the longitudinal groove to retain the pusher part 663 within the first reservoir 642.

To insert an aerosol-generating bead 1 into the aerosolisation chamber 616, a user manually pushes the slider 661 forward, i.e. towards the mouthpiece 614. The pusher part 663 is brought into engagement with the rearmost aerosol-generating bead 1 and the pushing force is transmitted along the plurality of beads to the foremost bead, i.e. the bead closest to the aerosolisation chamber 616. An aperture 674 is formed in the side wall of the aerosolisation chamber 616 adjacent the first reservoir 642 via which an aerosol-generating bead 1 may be inserted into the aerosolisation chamber 616. The aperture 674 is closeable by an inwardly opening door 668 hingedly attached to a side of the aperture 674. The door 668 is resiliently biased towards its closed configuration by a spring (not shown). If the force applied by a user to the slider 661 is sufficient to overcome the resilient force of the spring closing the door 668, the foremost aerosol-generating bead 1 will be pushed into the aerosolisation chamber 616. Once a bead 1 has been inserted into the aerosolisation chamber 616, the door 668 closes behind it under the action of the spring to prevent aerosol from escaping from the aerosolisation chamber 616. The front end wall of the first reservoir 642 is angled to direct the bead 1 into the aerosolisation chamber 616.

Following heating, a used bead 1b located within the aerosolisation chamber 616 remains in the aerosolisation chamber until a user is ready to insert the next bead 1. At which point, the user repeats the above-described process for inserting a bead 1. The action of inserting a new bead into the aerosolisation chamber 616 forces the used bead out of the aerosolisation chamber 616 via aperture 672 which is formed in an opposing side wall of the aerosolisation chamber 616 to aperture 674. Aperture 672 is closable by an outwardly opening door 666 hingedly attached to a side of the aperture 672. The door 666 is also resiliently biased towards its closed configuration by a spring (not shown). Once a bead has been ejected from the aerosolisation chamber 616, the door 666 closes behind it under the action of the spring to prevent aerosol from escaping from the aerosolisation chamber 616. Ejected beads 1b are stored in the second reservoir 644 which is also located within the housing 602 of the device 600 and extends longitudinally along an opposing side of the device 600 to the first reservoir 642. A closable opening (not shown) is provided in the second reservoir 644 to allow a user to empty the second reservoir once it is full of used beads 1b.

The invention claimed is:
1. An aerosol-generating system comprising:
   an aerosol-generating article, the aerosol-generating article comprising a single metered-dose of an aerosol-forming substrate, the metered-dose comprising an amount of the aerosol-forming substrate sufficient for generating an amount of aerosol for a single puff;
   an airflow pathway arranged between an air inlet and an air outlet;
   an aerosolisation chamber arranged at a location along the airflow pathway such that the airflow pathway passes through at least a portion of the aerosolisation chamber; and
   a flow controller for selectively controlling the flow of air through the airflow pathway, the flow controller having an open configuration in which air can flow into and out of the aerosolisation chamber and a closed configuration in which air is substantially prevented from flowing into and out of the aerosolisation chamber;
   wherein the aerosolisation chamber is configured to open to receive one aerosol-generating article at a time;

wherein the aerosolisation chamber is configured to close to contain the aerosol-generating article;

the aerosol-generating system further comprising:

a heating element arranged to heat the aerosolisation chamber when an aerosol-generating article is received within the aerosolisation chamber; and a guard for preventing the aerosol-generating article from leaving the aerolisation chamber via the airflow pathway, the guard comprising a mesh or a plate having at least one hole formed therethrough for preventing the aerosol-generating article from leaving the aerosolisation chamber via the airflow pathway whilst still permitting air to flow through the airflow pathway, wherein the mesh or plate is arranged across at least a portion of the airflow pathway;

wherein the aerosol-generating system is configured to heat the aerosolisation chamber containing the aerosol-generating article when the flow controller is in the closed configuration.

2. An aerosol-generating system according to claim 1, wherein the metered-dose of aerosol-forming substrate comprises about 2 to 30 mg of tobacco.

3. An aerosol-generating system according to claim 1, wherein the metered-dose of aerosol-forming substrate comprises about 100 lig of nicotine, a nicotine derivative or a nicotine analogue.

4. An aerosol-generating system according to claim 1, wherein the metered-dose of aerosol-forming substrate further comprises about 300 to 1250 μg of an aerosol-former.

5. An aerosol-generating system according to claim 1, wherein the aerosolisation chamber is sized to accommodate only one aerosol-generating article.

6. An aerosol-generating system according to claim 1, wherein a cross-sectional area of the aerosol-generating article is less than a cross-sectional area of the aerosolisation chamber such that air can flow around the aerosol-generating article and through the aerosolisation chamber.

7. An aerosol-generating system according to claim 6, wherein the cross-sectional area of the aerosol-generating article is between about 60 percent and 90 percent of the cross-sectional area of the aerosolisation chamber.

8. An aerosol-generating system according to claim 1, wherein the aerosolisation chamber comprises an aperture through which the aerosol-generating article can be loaded into the aerosolisation chamber, the system further comprising a closure for closing the aperture during heating of the aerosol-generating article.

9. An aerosol-generating system according to claim 1, wherein the system further comprises a delivery mechanism for delivering the aerosol-generating article into the aerosolisation chamber.

10. An aerosol-generating system according to claim 1, wherein the guard comprises a reduction in the cross-sectional area of the airflow pathway at the point the aerosolisation chamber is joined to the remainder of the airflow pathway.

11. An aerosol-generating system according to claim 1, wherein the system further comprises a storage unit for storing a plurality of single-use aerosol-generating articles.

12. A method of generating an aerosol, wherein the method is configured to generate the aerosol from an aerosol-generating article, the aerosol-generating article comprising a single metered dose of an aerosol-forming substrate, the metered-dose comprising an amount of the aerosol-forming substrate sufficient for generating an amount of aerosol for a single puff; the method comprising:

providing an airflow pathway between an air inlet and an air outlet;

providing an aerosolisation chamber arranged at a location along the airflow pathway such that the airflow pathway passes through at least a portion of the aerosolisation chamber;

providing a guard for preventing the aerosol-generating article from leaving the aerosolisation chamber via the airflow pathway, the guard comprising a mesh or a plate having at least one hole formed therethrough for preventing the aerosol-generating article from leaving the aerosolisation chamber via the airflow pathway whilst still permitting air to flow through the airflow pathway, wherein the mesh or plate is arranged across at least a portion of the airflow pathway;

opening the aerosolisation chamber;

placing one aerosol-generating article within the aerosolisation chamber;

closing the aerosolisation chamber to contain the aerosol-generating article;

closing the airflow pathway to substantially prevent air from flowing into and out of the aerosolisation chamber;

heating the aerosolisation chamber containing the aerosol-generating article such that the aerosol-forming substrate is aerosolised whilst the airflow pathway is closed, opening the airflow pathway such that a user can puff on the generated aerosol via the air outlet.

13. A method according to claim 12, wherein the method further comprises raising the temperature within the aerosolisation chamber to a predetermined temperature prior to placing the aerosol-generating article within the aerosolisation chamber.

14. A system according to claim 1, wherein the aerosol-generating article comprises an aerosol-generating bead; and wherein the aerosol-generating system further comprises: a reservoir for storing a plurality of aerosol-generating beads; and a delivery mechanism for individually delivering the plurality of aerosol-generating beads to the aerosolisation chamber of the aerosol-generating system.

15. A system according to claim 14, wherein the aerosol-generating system further comprises a second reservoir for storing used aerosol-generating beads that have been ejected from the aerosolisation chamber.

* * * * *